(12) United States Patent
Ghenne et al.

(10) Patent No.: US 11,266,731 B2
(45) Date of Patent: Mar. 8, 2022

(54) VACCINE

(71) Applicant: GlaxoSmithKline Biologicals SA, Rixensart (BE)

(72) Inventors: Laurence Danielle Ghenne, Rixensart (BE); Dominique Ingrid Lemoine, Rixensart (BE); Frédéric Mathot, Rixensart (BE); Florence Emilie Jeanne Francoise Wauters, Rixensart (BE)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 684 days.

(21) Appl. No.: 16/078,225

(22) PCT Filed: Feb. 20, 2017

(86) PCT No.: PCT/EP2017/053741
§ 371 (c)(1),
(2) Date: Aug. 21, 2018

(87) PCT Pub. No.: WO2017/144394
PCT Pub. Date: Aug. 31, 2017

(65) Prior Publication Data
US 2021/0187090 A1 Jun. 24, 2021

(30) Foreign Application Priority Data
Feb. 22, 2016 (GB) .................................... 1603029

(51) Int. Cl.
*A61K 39/09* (2006.01)
*A61K 39/00* (2006.01)

(52) U.S. Cl.
CPC .. *A61K 39/092* (2013.01); *A61K 2039/55505* (2013.01)

(58) Field of Classification Search
None
See application file for complete search history.

(56) References Cited

U.S. PATENT DOCUMENTS

2014/0105927 A1* 4/2014 Verlant ................ A61K 39/092
424/190.1

FOREIGN PATENT DOCUMENTS

| EP | WO 2014060385 | * | 4/2014 |
| WO | 2004081515 A2 | | 9/2004 |
| WO | 2006032499 A1 | | 3/2006 |

OTHER PUBLICATIONS

Jones et al, Journal of Biological Chemistry, vol. 280, No. 14, p. 13406-13414. (Year: 2005).*
PCT/EP2017/053741, May 5, 2017, International Search Report.
Kirkham et al., Infection and Immunity, 74(1): 586-593 (2006).
Pauksens et al., Clinical and Vaccine Immunology, 21(5): 651-660 (2014).
Michon et al., Vaccine, 16(18): 1732-1741 (1998).
Lindblad et al., Immunology and Cell Biology, 82(5): 497-505 (2004).
Huang et al., International Journal of Pharmaceutics, 466(1-2): 139-146 (2014).
Powell et al., Clinical and Experimental Vaccine Research, 4(1): 23-45 (2015).
Jones et al., Journal of Biological Chemistry, 280(14): 13406-13414 (2005).
Salha et al., Infection and Immunity, 80(6): 2212-2220 (2012).

* cited by examiner

*Primary Examiner* — Padmavathi Baskar

(57) ABSTRACT

The present invention is in the field of pneumococcal capsular saccharide conjugate vaccines. Specifically, the present invention relates to immunogenic compositions and vaccines comprising detoxified pneumolysin adsorbed onto aluminium phosphate and an improved process for the adsorption of detoxified pneumolysin onto aluminium phosphate. It additionally relates to the use of the immunogenic compositions and vaccines in the treatment or prevention of *Streptococcu pneumoniae* infection.

10 Claims, 3 Drawing Sheets

Specification includes a Sequence Listing.

Figure 1: Completeness of Adsorption
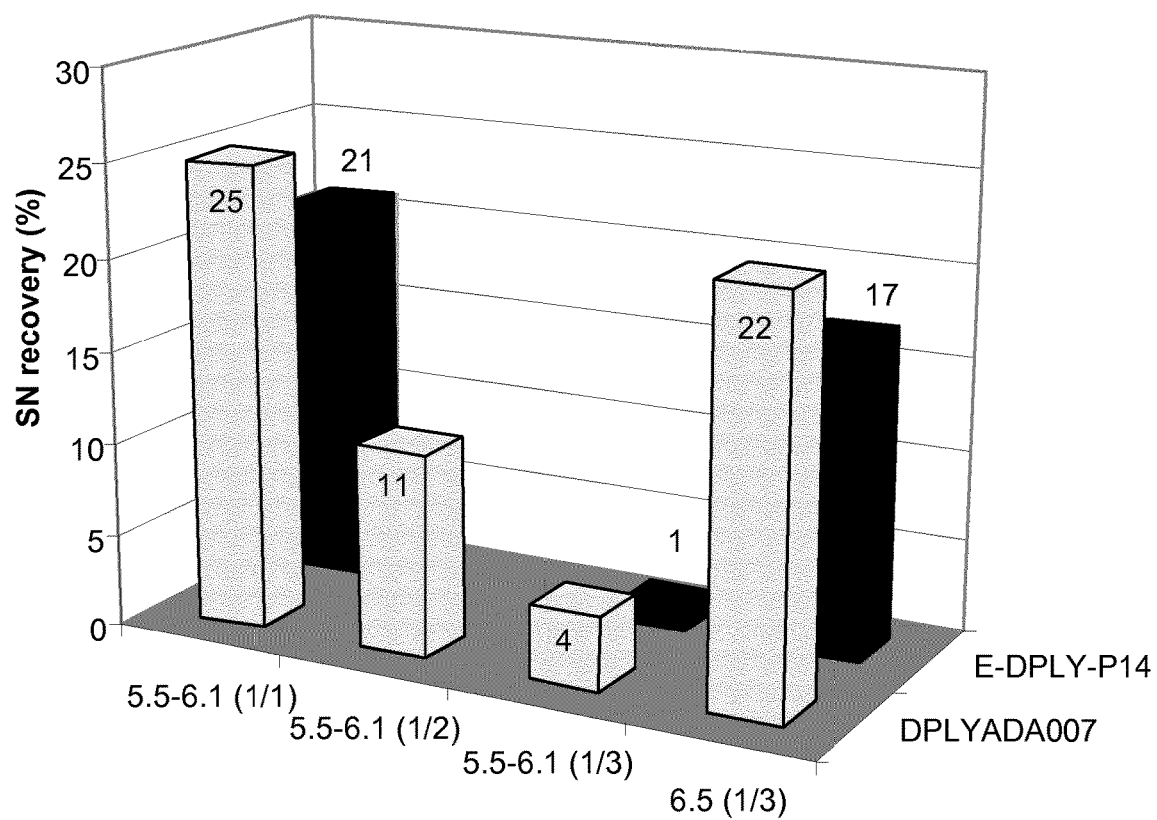

Figure 2: Antigenicity
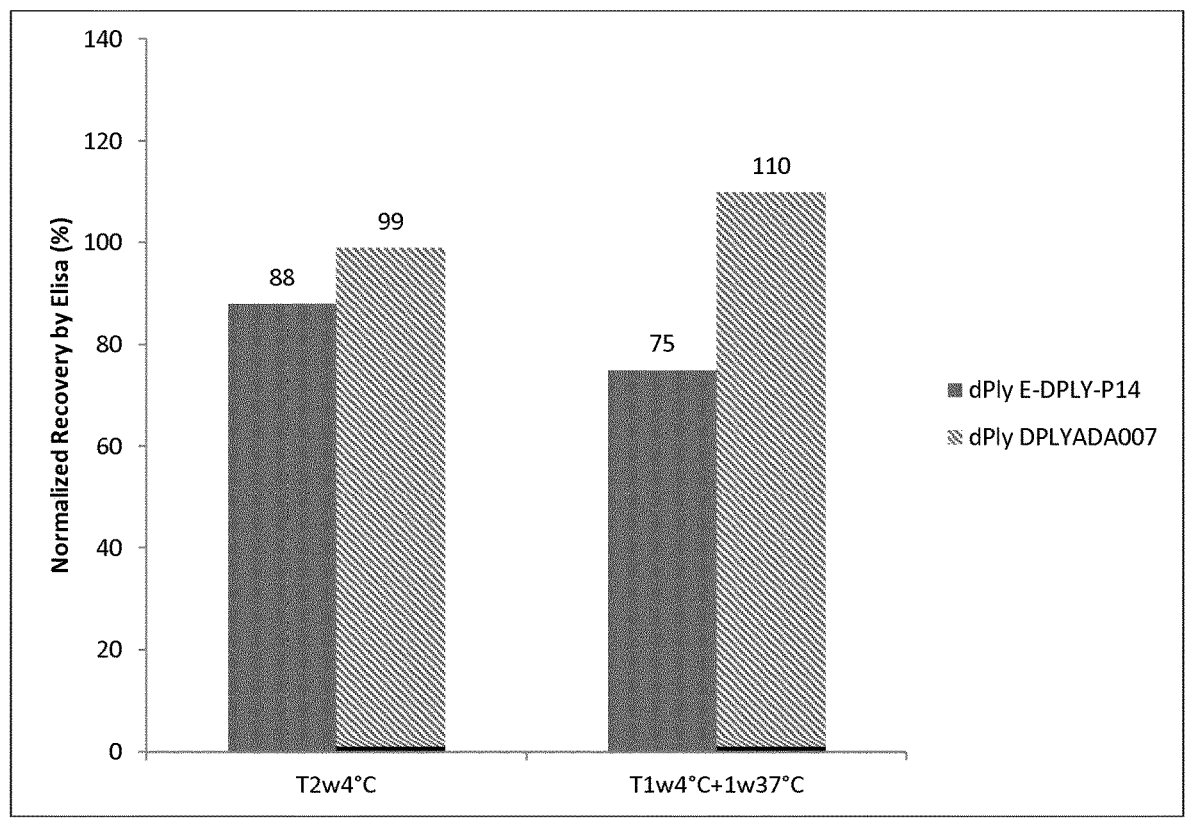

Figure 3: Particle size
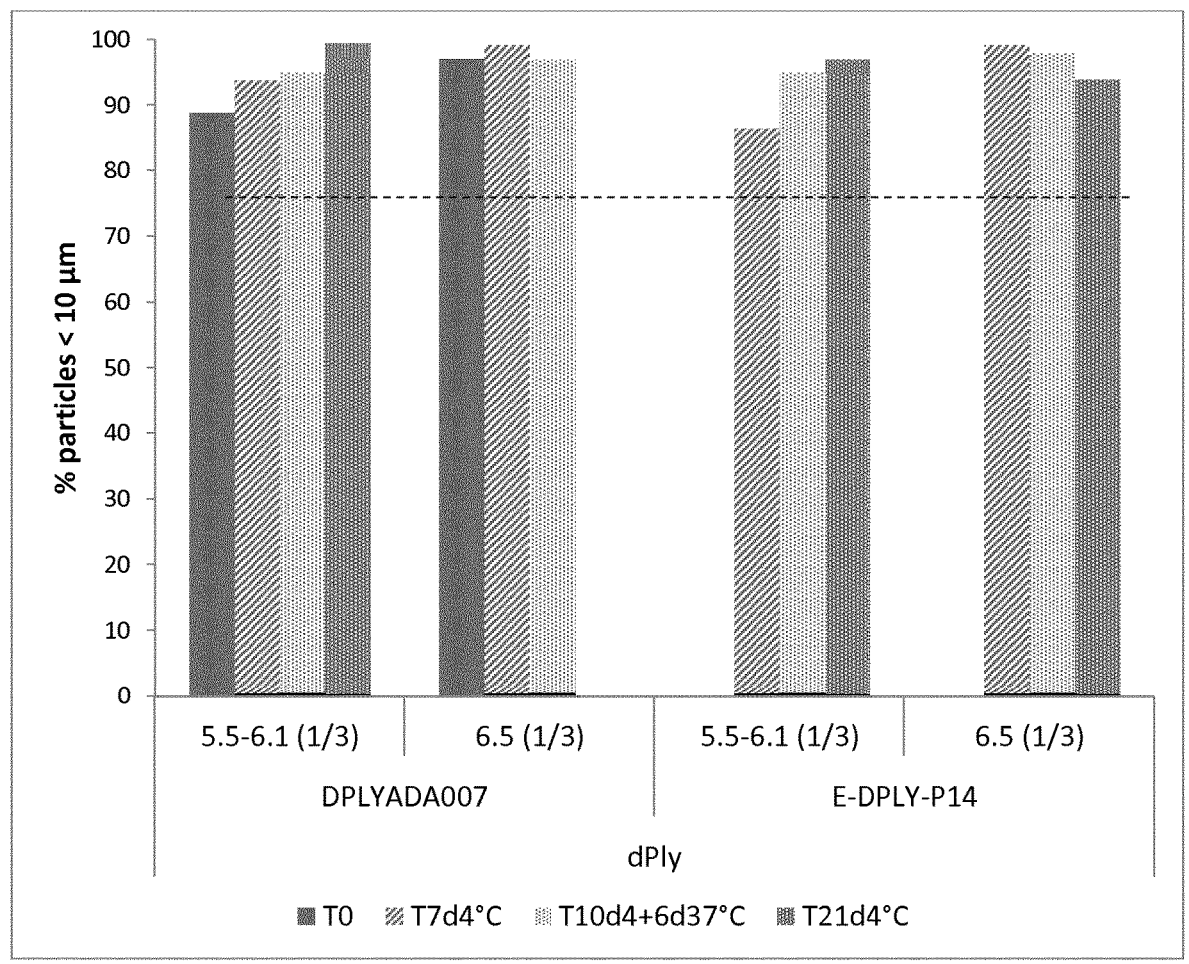

SEQUENCE LISTING

```
<160> NUMBER OF SEQ IDS NOS: 8

<210> SEQ ID NO 1
<211> LENGTH: 471
<212> TYPE: PRT
<213> ORGANISM: S. pneumoniae
<220> FEATURE:
<223> OTHER INFORMATION: Pneumolysin protein from S. pneumoniae

<400> SEQUENCE: 1
```

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu

```
                        165                 170                 175
Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
        210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 2
<211> LENGTH: 471
<212> TYPE: PRT
<213> ORGANISM: S. pneumoniae
<220> FEATURE:
<223> OTHER INFORMATION: Pneumolysin protein from S. pneumoniae

<400> SEQUENCE: 2

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
```

```
                50                  55                  60
Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
                130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
                195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
                290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asn Glu Leu Ser Tyr
                370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Leu Tyr Pro Gln Val
450                 455                 460

Glu Asp Lys Val Glu Asn Asp
465                 470
```

<210> SEQ ID NO 3
<211> LENGTH: 471
<212> TYPE: PRT
<213> ORGANISM: S. pneumoniae
<220> FEATURE:
<223> OTHER INFORMATION: Pneumolysin protein from S. pneumoniae

<400> SEQUENCE: 3

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365
```

```
Gly Ala Tyr Val Ala Gln Tyr Tyr Ile Thr Trp Asp Glu Leu Ser Tyr
            370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
            450                 455                 460

Glu Asp Lys Val Glu Asn Asp
465                 470

<210> SEQ ID NO 4
<211> LENGTH: 471
<212> TYPE: PRT
<213> ORGANISM: S. pneumoniae
<220> FEATURE:
<223> OTHER INFORMATION: Pneumolysin protein from S. pneumoniae

<400> SEQUENCE: 4

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255
```

```
Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 5
<211> LENGTH: 471
<212> TYPE: PRT
<213> ORGANISM: S. pneumoniae
<220> FEATURE:
<223> OTHER INFORMATION: Pneumolysin protein from S. pneumoniae

<400> SEQUENCE: 5

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140
```

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
            325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 6
<211> LENGTH: 364
<212> TYPE: PRT
<213> ORGANISM: H. influenzae
<220> FEATURE:
<223> OTHER INFORMATION: Protein D from H. influenzae

<400> SEQUENCE: 6

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
    290                 295                 300

Val Lys Glu Leu Ala Gln Tyr Asn Val Glu Val His Pro Tyr Thr Val
305                 310                 315                 320

Arg Lys Asp Ala Leu Pro Glu Phe Phe Thr Asp Val Asn Gln Met Tyr
                325                 330                 335

Asp Ala Leu Leu Asn Lys Ser Gly Ala Thr Gly Val Phe Thr Asp Phe
            340                 345                 350

Pro Asp Thr Gly Val Glu Phe Leu Lys Gly Ile Lys
        355                 360

<210> SEQ ID NO 7
<211> LENGTH: 348
<212> TYPE: PRT
<213> ORGANISM: Artificial
<220> FEATURE:
<223> OTHER INFORMATION: Tripeptide MDP from NS1 fused to N-terminal of
      protein D from H. influenzae

<400> SEQUENCE: 7

Met Asp Pro Ser Ser His Ser Ser Asn Met Ala Asn Thr Gln Met Lys
1               5                   10                  15

Ser Asp Lys Ile Ile Ile Ala His Arg Gly Ala Ser Gly Tyr Leu Pro

```
                    20                  25                  30
        Glu His Thr Leu Glu Ser Lys Ala Leu Ala Phe Ala Gln Gln Ala Asp
                    35                  40                  45

Tyr Leu Glu Gln Asp Leu Ala Met Thr Lys Asp Gly Arg Leu Val Val
         50                  55                  60

Ile His Asp His Phe Leu Asp Gly Leu Thr Asp Val Ala Lys Lys Phe
         65                  70                  75                  80

Pro His Arg His Arg Lys Asp Gly Arg Tyr Tyr Val Ile Asp Phe Thr
                        85                  90                  95

Leu Lys Glu Ile Gln Ser Leu Met Thr Glu Asn Phe Glu Thr Lys
                       100                 105                 110

Asp Gly Lys Gln Ala Gln Val Tyr Pro Asn Arg Phe Pro Leu Trp Lys
                       115                 120                 125

Ser His Phe Arg Ile His Thr Phe Glu Asp Glu Ile Glu Phe Ile Gln
                       130                 135                 140

Gly Leu Glu Lys Ser Thr Gly Lys Lys Val Gly Ile Tyr Pro Glu Ile
        145                 150                 155                 160

Lys Ala Pro Trp Phe His His Gln Asn Gly Lys Asp Ile Ala Ala Glu
                       165                 170                 175

Thr Leu Lys Val Leu Lys Lys Tyr Gly Tyr Asp Lys Lys Thr Asp Met
                       180                 185                 190

Val Tyr Leu Gln Thr Phe Asp Phe Asn Glu Leu Lys Arg Ile Lys Thr
                       195                 200                 205

Glu Leu Leu Pro Gln Met Gly Met Asp Leu Lys Leu Val Gln Leu Ile
        210                 215                 220

Ala Tyr Thr Asp Trp Lys Glu Thr Gln Glu Lys Asp Pro Lys Gly Tyr
        225                 230                 235                 240

Trp Val Asn Tyr Asn Tyr Asp Trp Met Phe Lys Pro Gly Ala Met Ala
                       245                 250                 255

Glu Val Val Lys Tyr Ala Asp Gly Val Gly Pro Gly Trp Tyr Met Leu
                       260                 265                 270

Val Asn Lys Glu Glu Ser Lys Pro Asp Asn Ile Val Tyr Thr Pro Leu
                       275                 280                 285

Val Lys Glu Leu Ala Gln Tyr Asn Val Glu Val His Pro Tyr Thr Val
                       290                 295                 300

Arg Lys Asp Ala Leu Pro Glu Phe Phe Thr Asp Val Asn Gln Met Tyr
        305                 310                 315                 320

Asp Ala Leu Leu Asn Lys Ser Gly Ala Thr Gly Val Phe Thr Asp Phe
                       325                 330                 335

Pro Asp Thr Gly Val Glu Phe Leu Lys Gly Ile Lys
                       340                 345

<210> SEQ ID NO 8
<211> LENGTH: 10
<212> TYPE: PRT
<213> ORGANISM: H. influenzae
<220> FEATURE:
<223> OTHER INFORMATION: Fragment of protein D from H. influenzae

<400> SEQUENCE: 8

Ser Ser His Ser Ser Asn Met Ala Asn Thr
1               5                   10
```

VACCINE

CROSS-REFERENCE TO RELATED APPLICATIONS

This application is filed pursuant to 35 U.S.C. § 371 as a United States National Phase Application of International Application No. PCT/EP2017/053741 filed Feb. 20, 2017 which claims priority from GB 1603029.8 filed Feb. 22, 2016.

SEQUENCE LISTING

A sequence listing filed herewith, entitled "VB66043 Seq Listing 11_22_2021", prepared Nov. 22, 2021, 26.8 KB in size, is hereby incorporated by reference herein.

FIELD OF THE INVENTION

The present invention relates to immunogenic compositions and vaccines comprising detoxified pneumolysin adsorbed onto aluminium phosphate and an improved process for the adsorption of detoxified pneumolysin onto aluminium phosphate. It additionally relates to the use of the immunogenic compositions and vaccines comprising detoxified pneumolysin adsorbed onto aluminium phosphate in the treatment or prevention of Streptococcu pneumoniae infection.

BACKGROUND OF THE INVENTION

Streptococcu pneumoniae (S. pneumoniae) is a Gram-positive bacterium responsible for considerable morbidity and mortality (particularly in infants and the elderly), causing invasive diseases such as bacteraemia and meningitis, pneumonia and other non-invasive diseases, such as acute otitis media. About 800,000 children die annually due to pneumococcal disease, especially in emerging countries (O-Brien et al. 2009 Lancet 374:893-902). The increasing number of antibiotic-resistant strains (Linares et al. 2010 Cin. Microbiol. Infect. 16:402-410) and the severity of pneumococcal diseases make vaccination the most effective intervention.

The major clinical syndromes caused by S. pneumoniae are widely recognized and discussed in standard medical textbooks (Fedson D S, Muscher D M. In: Plotkin S A, Orenstein W A, editors. Vaccines. 4th edition. PhiladelphiaWB Saunders Co, 2004a: 529-588). For instance, Invasive Pneumococcal Disease (IPD) is defined as any infection in which S. pneumoniae is isolated from the blood or another normally sterile site (Musher D M. Streptococcu pneumoniae. In Mandell G L, Bennett J E, Dolin R (eds). Principles and Practice of Infectious diseases (5th ed). New York, Churchill Livingstone, 2001, p2128-2147). Chronic obstructive pulmonary disease (COPD) is recognised as encompassing several conditions (airflow obstruction, chronic bronchitis, bronchiolitis or small airways disease and emphysema) that often coexist (Wilson et al., Eur. Respir. J. 2001; 17: 995-1007). Patients suffer exacerbations of COPD that are usually associated with increased breathlessness, and often have increased cough that may be productive of mucus or purulent sputum (Wilson, Eur Respir J 2001 17:995-1007). COPD is defined physiologically by the presence of irreversible or partially reversible airway obstruction in patients with chronic bronchitis and/or emphysema (Standards for the diagnosis and care of patients with chronic obstructive pulmonary disease. American Thoracic Society. Am J Respir Crit Care Med. 1995 November.; 152(5 Pt 2):S77-121). Exacerbations of COPD are often caused by bacterial (e.g. pneumococcal) infection (Sethi S, Murphy T F. Bacterial infection in chronic obstructive pulmonary disease in 2000: a state-of-the-art review. Clin Microbiol Rev. 2001 April; 14(2):336-63).

Streptococcu pneumoniae, also referred to as pneumococcus, is encapsulated with a chemically linked polysaccharide which confers serotype specificity. There are more than 90 known serotypes of pneumococci, and the capsule is the principle virulence determinant for pneumococci, as the capsule not only protects the inner surface of the bacteria from complement, but is itself poorly immunogenic. An anti-polysaccharide antibody level has been regarded as predictive of the protection against invasive pneumococcal disease (Jodar et al. Vaccine, (21) 2003, p. 3264-3272). After initial licensure of a 7-valent conjugate vaccine containing serotypes 4, 6B, 9V, 14, 18C, 19F, 23F (PCV7), two pneumococcal conjugate vaccines (PCVs) designed to broaden coverage have been licensed. The 10-valent pneumococcal Haemophilus influenzae protein D conjugate vaccine (PCV10) contains serotypes 1, 4, 5, 6B, 7F, 9V, 14 and 23F conjugated to nontypeable H. influenzae protein D, plus serotype 18C conjugated to tetanus toxoid and serotype 19F conjugated to diphtheria toxoid. The 13-valent pneumococcal conjugate vaccine (PCV13) contains the PCV7 (4, 6B, 9V, 14, 18C, 19F, 23F) serotypes plus serotypes 1, 3, 5, 6A, 7F and 19A, conjugated to cross-reactive material CRM197. It is an object of the present invention to develop improved Streptococcu pneumoniae vaccines.

Pneumolysin (ply) is a 53 kDa thiol-activated cytolysin found in all strains of S. pneumoniae, which is released on autolysis and contributes to the pathogenesis of S. pneumoniae. It is highly conserved with only a few amino acid substitutions occurring between the ply proteins of different serotypes. Pneumolysin is a multifunctional toxin with a distinct cytolytic (hemolytic) and complement activation activities (Rubins et al., Am. Respi. Cit Care Med, 153: 1339-1346 (1996)). The toxin is not secreted by pneumococci, but it is released upon lysis of pneumococci under the influence of autolysin. Its effects include, for example, the stimulation of the production of inflammatory cytokines by human monocytes, the inhibition of the beating of cilia on human respiratory epithelial, the decrease of bactericidal activity and migration of neutrophils, and in the lysis of red blood cells, which involves binding to cholesterol. Expression and cloning of wild-type or native pneumolysin is described in Walker et al. (Infect Immun, 55:1184-1189 (1987)), Mitchell et al. (Biochim Biophys Acta, 1007:67-72 (1989) and Mitchell et al (NAR, 18:4010 (1990)).

The present invention provides detoxified pneumolysin adsorbed onto aluminium phosphate having improved properties and an improved process for the adsorption of detoxified pneumolysin onto aluminium phosphate. The present inventors have found that by admixing detoxified pneumolysin and aluminium phosphate at a specific pH range a high level of completeness of adsorption may be obtained (greater than 85%), and an adsorbed detoxified pneumolysin having desirable properties, for example in relation to particle size, can be produced. The particle size of the adsorbed detoxified pneumolysin and level of adsorption can affect immunogenicity; therefore, a particle size <10 μm and a high level of adsorption (greater than 85%) are desirable. Furthermore, the present inventors have found that it is advantageous to pre-adsorb detoxified pneumolysin onto aluminium phosphate according to the method of invention prior to mixing with other antigens. For example, preadsorbed detoxified pneumolysin may be mixed with pre-adsorbed PhtD which has been adsorbed onto aluminium phosphate under different conditions.

BRIEF DESCRIPTION OF FIGURES

FIG. 1 Evaluation of Completeness of Adsorption. Compares completeness of adsorption of detoxified pneumolysin (dPly) onto aluminium phosphate under different pHs and ratios of dPly:$Al^{3+}$ (from aluminium phosphate) (i) pH5.5-6.1 and ratio 1:1, (ii) pH5.5-6.1 and ratio 1:2, (iii) pH5.5 to 6.1, ratio 1:3, and (iv) pH6.5 and ratio 1:3. Two different antigen lots were tested: E-DPLY-P14 and DPLYADA007.

FIG. 2 Antigenicity. Shows Elisa recovery for dPly adsorbed onto aluminium phosphate at pH5.5 to 6.1, ratio of dPly:$Al^{3+}$ (from aluminium phosphate) of 1:3. The bars correspond to the two different antigen lots prepared according to the method of Example 1: the bars on the left correspond to dPly E-DPLY-P14 and the bars on the right correspond to dPly DPLYADA007. The dPly was stored either for 2 weeks at 4° C. (T2w4° C.) or 1 week at 4° C. followed by 1 week at 37° C. (T1w4° C+1w37° C.). Note: this figure has been corrected to show that dPly DPLYADA007 had a recovery of 110% by Elisa after 1 week at 4° C. followed by 1 week at 37° C. (T1w4° C+1w37° C.).

FIG. 3 Particle size. Compares the percentage of particles of dPly adsorbed onto aluminium phosphate less than 10μm for under different pH and ratios of dPly:$Al^+$ (from aluminium phosphate): (i) pH5.5-6.1 and ratio 1:1 and (ii) pH5.5 to 6.1 and ratio 1:3. The bars from left to right correspond to T0 (time=zero), T7d4° C. (7 days at 4° C.), T7d37° C. (7 days at 37° C.), T10d4+6d37° C. (10 days at 4° C. and 6 days at 37° C.) and T21d4° C. (21 days at 4° C.). Data for the two different antigen lots is shown: dPly E-DPLY-P14 on the right and dPly DPLYADA007 on the left.

DESCRIPTION OF THE INVENTION

The present invention provides an immunogenic composition comprising detoxified pneumolysin having a high level of adsorption (greater than 85%) onto aluminium phosphate. The present invention also provides an improved process for adsorption of detoxified pneumolysin onto aluminium phosphate.

Accordingly, in the first aspect of the present invention, there is provided an immunogenic composition or vaccine comprising detoxified pneumolysin adsorbed onto an aluminium phosphate, wherein more than 85% (suitably more than 90%, 91%, 92%, 93%, 94%, 95%, 96%, 97%, 98% or 99%) of the detoxified pneumolysin is adsorbed onto the aluminium phosphate.

In another aspect, the present invention provides a process for adsorption of detoxified pneumolysin onto an aluminium phosphate comprising the step of (i) admixing detoxified pneumolysin and the aluminium phosphate at a pH less than 6.5 (e.g. less than 6.4, less than 6.3, less than 6.2, less than 6.1), suitably less than pH 6.0, for example pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, or pH 5.4 to 5.6 (e.g. pH 5.5). Unless otherwise stated, such ranges are inclusive of the end points. In another embodiment, the pH is pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, or pH 5.4 to 5.6 not including the end points.

In a further aspect of the invention, there is provided a method for the treatment or prevention of *Streptococcu pneumoniae* infection in a subject in need thereof comprising administering to said subject a therapeutically effective amount of an immunogenic composition or vaccine of the invention.

In a further aspect of the invention, there is provided immunogenic composition or vaccine of the invention for use in the treatment or prevention of disease caused by Streptococcus pneumoniae infection.

The term "fragment" as used in this specification is a portion smaller than the whole that is capable of eliciting a humoral and/or cellular immune response in a host animal, e.g. human. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Typically, fragments comprise at least 10, 20, 30, 40 or 50 contiguous amino acids of the full length sequence. Fragments may be readily modified by adding or removing 1, 2, 3, 4, 5, 6, 7, 8, 9, 10, 20, 30, 40 or 50 amino acids from either or both of the N and C termini.

The term "conservative amino acid substitution" as used in this specification involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" as used in this specification is the removal of one or more amino acid residues from the protein sequence. Typically, no more than about from 1 to 6 residues (e.g. 1 to 4 residues) are deleted at any one site within the protein molecule.

The term "insertion" as used in this specification is the addition of one or more non-native amino acid residues in the protein sequence. Typically, no more than about from 1 to 6 residues (e.g. 1 to 4 residues) are inserted at any one site within the protein molecule.

As used herein, the term "treatment" (including variations thereof, e.g. "treat" or "treated") means any one or more of the following: (i) the prevention of infection or re-infection, (ii) the reduction in the severity of, or, in the elimination of symptoms, (iii) the delay in recurrence of symptoms, and (iii) the substantial or complete elimination of the pathogen or disorder in a subject. Hence, treatment may be effected prophylactically (prior to infection) or therapeutically (following infection).

For the purposes of this invention, "treatment or prevention of exacerbations of COPD" or "reduction in severity of COPD exacerbations" refers to a reduction in incidence or rate of COPD exacerbations (for instance a reduction in rate of 0.1, 0.5, 1, 2, 5, 10, 20% or more) or a reduction in severity of COPD exacerbations (e.g. airflow obstruction, chronic bronchitis, bronchiolitis or small airways disease and emphysema), for instance within a patient group immunized with the immunogenic compositions or vaccines of the invention.

Pneumolysin

By "pneumolysin", or "ply" or "Ply", it is meant: native or wild-type pneumolysin from pneumococcus or recombinant pneumolysin having the sequence of native or wild-type pneumolysin. Expression and cloning of wild-type or native pneumolysin is known in the art. See, for example, Walker et al. (Infect Immun, 55:1184-1189 (1987)), Mitchell et al. (Biochim Biophys Acta, 1007:67-72 (1989) and Mitchell et al (NAR, 18:4010 (1990)). WO2010/071986 describes wild-type Ply, e.g. SEQ ID NOs 2-42 (for example SEQ ID NOs 34, 35, 36, 37, 41). Furthermore, EP1601689B1 describes methods for purifying bacterial cytolysins such as pneumococcal pneumolysin by chromatography in the presence of detergent and high salt. In an embodiment, native or wild-type pneumolysin from pneumococcus or recombinant pneumolysin having the sequence of native or wild-type pneumolysin is used to generate detoxified pneumolysin. In one aspect, pneumolysin used to generate detoxified pneumolysin has the sequence of Seq ID No. 1 (Seq ID No. 34 of WO2010/071986). In another aspect, pneumolysin used to generate detoxified pneumolysin has the sequence of Seq ID No. 2 (Seq ID No. 35 of WO2010/071986). In another aspect, pneumolysin used to generate detoxified pneumolysin has the sequence of Seq ID No. 3 (Seq ID No. 36 of WO2010/071986). In another aspect, pneumolysin used to generate detoxified pneumolysin has the sequence of Seq ID No. 4 (Seq ID No. 37 of WO2010/071986). In another aspect, pneumolysin used to generate detoxified pneumolysin has the sequence of Seq ID No. 5 (Seq ID No. 41 of WO2010/071986).

In an embodiment, the pneumolysin used to generate detoxified pneumolysin includes fragments and/or variants, having differences in nucleic acid or amino acid sequences as compared to a wild type sequence (e.g. Seq ID Nos 1-5).

Where fragments of pneumolysin are used, these fragments will be at least about 15, at least about 20, at least about 40, or at least about 60 contiguous amino acid residues in length. In an embodiment of the invention, immunogenic fragments of pneumolysin comprise at least about 15, at least about 20, at least about 40, or at least about 60 contiguous amino acid residues of the full length sequence, wherein said polypeptide is capable of eliciting an immune response specific for said amino acid sequence. Native pneumolysin is known to consist of four major structural domains (Rossjohn et al. Cell. 1997 May 30; 89(5):685-92). These domains may be modified by removing and/or modifying one or more of these domains. In an embodiment, the or each fragment contains exactly or at least 1, 2 or 3 domains. In another embodiment, the or each fragment contains exactly or at least 2 or 3 domains. In another embodiment, the or each fragment contains at least 3 domains. The or each fragment may be more than 50, 60, 70, 80, 90 or 100% identical to a wild type pneumolysin sequence.

In accordance with the present invention, a variant of pneumolysin is a protein in which the native pneumolysin is mutated. The term "mutated" is used herein to mean pneumolysin which has undergone deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. Variants of pneumolysin typically include any pneumolysin or any fragment of pneumolysin which shares at least 80, 90, 94, 95, 98, or 99% amino acid sequence identity with a wild-type pneumolysin sequence, for example a wild-type pneumolysin sequence disclosed in WO2010/071986. In an embodiment, variants of pneumolysin typically include any pneumolysin or any fragment of pneumolysin which shares at least 80, 90, 94, 95, 96, 97, 98, or 99% amino acid sequence identity with SEQ ID NO: 1. In an embodiment, variants of pneumolysin typically include any pneumolysin or any fragment of pneumolysin which shares at least 80, 90, 94, 95, 96, 97, 98, or 99% amino acid sequence identity with SEQ ID NO: 2. In an embodiment, variants of pneumolysin typically include any pneumolysin or any fragment of pneumolysin which shares at least 80, 90, 94, 95, 96, 97, 98, or 99% amino acid sequence identity with SEQ ID NO: 3. In an embodiment, variants of pneumolysin typically include any pneumolysin or any fragment of pneumolysin which shares at least 80, 90, 94, 95, 96, 97, 98, or 99% amino acid sequence identity with SEQ ID NO: 4. In an embodiment, variants of pneumolysin typically include any pneumolysin or any fragment of pneumolysin which shares at least 80, 90, 94, 95, 96, 97, 98, or 99% amino acid sequence identity with SEQ ID NO: 5. In an embodiment, the present invention includes fragments and/or variants in which several, 5 to 10, 1 to 5, 1 to 3, 1 to 2 or 1 amino acids are substituted, deleted, or added in any combination. In another embodiment, the present invention includes fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]). Variants of pneumolysin are described for example in WO04/43376, WO05/108580, WO05/076696, WO10/071986, WO10/109325 (SEQ ID NOs 44, 45 and 46) and WO10/140119 (SEQ ID NOs 50 and 51). In an embodiment, the immunogenic composition of the invention comprises a variant of pneumolysin, for example, those described in WO05/108580, WO05/076696, WO10/071986.

In an embodiment of the invention, the pneumolysin and its fragments and/or variants thereof, used to generate detoxified pneumolysin, have an amino acid sequence sharing at least 80, 85, 90, 95, 96, 97, 98, 99 or 100% identity with the wild type sequence for pneumolysin, e.g. SEQ ID NOs 1, 2, 3, 4 or 5. In another embodiment of the invention, pneumolysin and its fragments and/or variants thereof, comprise at least about 15, at least about 20, at least about 40, or at least about 60 contiguous amino acid residues of the wild type sequence for pneumolysin, e.g. of SEQ ID NOs 1, 2, 3, 4 or 5.

Because pneumolysin is a toxin, it needs to be detoxified (i.e. rendered non-toxic to a mammal, e.g. human, when provided at a dosage suitable for protection) before it can be administered in vivo. As used herein, it is understood that the term "detoxified pneumolysin" or "dPly" refers to detoxified pneumolysin suitable for medical use (i.e. non toxic when provided to a mammal, e.g. human at a dosage suitable for protection). Pneumolysin may be detoxified chemically and/or genetically. Therefore, immunogenic compositions of the invention comprise detoxified pneumolysin (dPly).

Detoxification of pneumolysin can be conducted by chemical means, e.g. using a crosslinking agent, such as formaldehyde, glutaraldehyde and a cross-linking reagent containing an N-hydroxysuccinomido ester and/or a maleimide group (e.g. GMBS) or a combination of these, see for example EP1601689B1, WO04/081515, WO2006/032499. The pneumolysin subject to chemical detoxification may be a native or recombinant protein or a protein that has been genetically engineered to reduce its toxicity (see below). Fragments and/or variants of pneumolysin may also be detoxified by chemical means. In an embodiment, immunogenic compositions of the invention may comprise pneumolysin which has been chemically detoxified, e.g. by a formaldehyde treatment. For example, pneumolysin may be purified and detoxified as described in WO2004/081515. Detoxification of pneumolysin using formaldehyde may be carried out using formaldehyde in the presence of L-lysine, for example by treatment of purified pneumolysin (ply) with 50 mM L-lysine and 0.1% formaldehyde (w/v) for 21 days at 40° C.

Pneumolysin can also be genetically detoxified. Thus, the invention encompasses pneumococcal proteins which may be, for example, mutated proteins (as defined herein).

In one embodiment, the molecule has undergone deletion or substitution of 1-15 or any subset thereof, for example, 10-15 amino acids. The mutated sequences may remove undesirable activities such as membrane permeation, cell lysis, and cytolytic activity against human erythrocytes and other cells, in order to reduce the toxicity, whilst retaining the ability to induce anti-pneumolysin protective and/or neutralizing antibodies following administration to a human. Fusion proteins of pneumolysin or fragments and/or variants of pneumolysin may also be detoxified by genetic means. For example, as described herein, a mutant pneumolysin protein may be altered so that it is biologically inactive whilst still maintaining its immunogenic epitopes, see, for example, WO90/06951, Berry et al. (Infect Immun, 67:981-985 (1999)) and WO99/03884. Alternatively, a pneumolysin protein may be detoxified by three amino acid substitutions comprising $T_{65}$ to C, $G_{293}$ to C and $C_{428}$ to A as described in WO2010/071986. For example, one of SEQ ID NOs 1 to 5 could be detoxified by three amino acid substitutions comprising T65 to C, G293 to C and C428 to A. Another example of a genetically detoxified pneumolysin that can be used in the present invention is SEQ ID NO: 9 from WO2011/075823. In another aspect, the modified pneumolysin protein of the invention may be detoxified by amino acid substitutions as described in Taylor et al. PLOS ONE 8(4): e61300 (2013), for example $A_{370}$ to E, $W_{433}$ to E and/or $L_{460}$ to E. Thus, in a further embodiment, immunogenic compositions of the invention may comprise pneumolysin which has been genetically detoxified. A combination of techniques may also be used to detoxify pneumolysin. For example, immunogenic compositions of the invention may comprise pneumolysin which has been chemically and genetically detoxified.

In one aspect the detoxified pneumolysin is conjugated to a saccharide, e.g. a capsular saccharide of *S. pneumoniae*. For example, pneumolysin may be conjugated to a capsular saccharide of *S. pneumoniae* selected from serotypes 1, 2, 3, 4, 5, 6A, 6B, 7F, 8, 9N, 9V, 10A, 11A, 12F, 14, 15, 17F, 18C, 19A, 19F, 20, 22F, 23F and 33F. In a particular aspect, pneumolysin may be conjugated to capsular saccharide of *S. pneumoniae* serotype 19A. In another aspect, the pneumococcal protein is unconjugated or present in the immunogenic composition as a free protein.

Aluminium Phosphate

Immunogenic compositions of the invention include an aluminium phosphate adjuvant. Aluminium phosphate (including both anhydrous and hydrated forms) is often referred to for convenience as "$AlPO_4$", although hydrated forms (hydroxyphosphates) can be distinguished from anhydrous $AlPO_4$ by the presence of hydroxyl groups $(Al(OH)_x(PO_4)_y$, e.g. $Al(OH)(PO_4))$. In one aspect of the invention, the aluminium phosphate is aluminium hydroxyphosphate (e.g. amorphous aluminium hydroxyphosphate). In another aspect of the invention, the aluminium phosphate is aluminium orthophosphate (also known as "aluminium monophopshate"). Aluminium phosphate adjuvants may be purchased from Brenntag, e.g. aluminium phosphate gel adjuvant.

Aluminium phosphate can be a precipitate of insoluble aluminium phosphate (amorphous, semi-crystalline or crystalline) which may be prepared by mixing soluble aluminium salts and phosphoric acid salts, e.g. sodium phosphate or potassium phosphate. In one aspect, the aluminium phosphate is amorphous (e.g. amorphous hydroxyphosphate). Aluminium hydroxyphosphate is not a stoichiometric compound and its hydroxyl and phosphate composition depends on precipitation reactants and conditions. The Phosphate:Aluminium (P:Al) weight/weight (w/w) of an aluminium hydroxyphosphate adjuvant will generally be between 2:1 to 4:1, suitably between 2.5:1 to 3.5:1, or between 3:1 to 3.5:1. The aluminium content may be determined by atomic absorption spectrophotometry with nitrous flame, see for example May et al. (1984) J. Biol. Stand. 12(2):175-83.

In one embodiment, the aluminium phosphate used in the process of the invention comprises NaCl, suitably 0.8% to 1.0%, e.g. 0.9% (w/w).

In an embodiment, the aluminium phosphate used in the process of the invention has a pH between 4.8 and 6.2. In another embodiment, the aluminium phosphate used in the process of the invention has a pH between 5.5 and 6.1. In another embodiment, the aluminium phosphate used in the process of the invention has a pH between 4.8 and 5.8. In another embodiment, the aluminium phosphate used in the process of the invention has a pH between 5.2 and 5.8.

In one embodiment, the aluminium phosphate used in the process of the invention is "extra-washed" prior to the adsorption of dPly such that the free phosphate ion concentration is reduced to below 10 mM (e.g. 3 mM or less, 2.5 mM or less). For example, the phosphate ions may be removed either by repeated centrifugation (e.g. at least 3 times) and dilution steps (i.e. removal of the supernatant and resuspension of the pellet in saline), or by diafiltration steps.

In another embodiment, the aluminium phosphate should be sterilised before adsorption of antigen. In one aspect, the aluminium phosphate is sterilised by autoclaving. In another aspect the aluminium phosphate is sterilised by irradiation, e.g. using ultra violet (UV) light.

Completeness of adsorption of a protein antigen (e.g. dPly) onto aluminium phosphate can be measured by measuring the supernatant (SN) of centrifuged samples via Lowry and comparing the total amount of protein in the sample (measured before adsorption occurs or by desorbing adsorbed antigen) to the amount which remains in the supernatant after centrifugation, as described in Example 2 herein. This methodology is further described in Chapter 4 of Methods in Molecular Medicine, Vol. 42 (edited by D. T. O-Hagan) Vaccine Adjuvants Preparation Methods and Research Protocols. In one aspect, the present invention provides detoxified pneumolysin adsorbed onto aluminium phosphate, wherein more than 85% (suitably more than 90%, 91%, 92%, 93%, 94%, 95%, 96%, 97%, 98% or 99%) of the dPly is adsorbed onto the aluminium phosphate. In one aspect of the invention, completeness of adsorption is measured on the day of formulation (TO). In another aspect of the invention, completeness of adsorption is measured after 7 days at +4° C. (T7d4° C.) following formulation. In another aspect of the invention, completeness of adsorption is measured after 21 days at +4° C. (T21d4° C.) following formulation. In another aspect of the invention, completeness of adsorption is measured after 7 days under accelerated conditions, e.g. 7 days at 37° C. (7d37° C.) following formulation. In another aspect of the invention, completeness of adsorption is measured after 16 days under accelerated conditions, e.g. 10 days at 4° C. followed by 6 days at 37° C. (T10d4° C+6d37° C.) following formulation.

Particle size of a protein antigen (e.g. dPly) adsorbed onto aluminium phosphate, can be measured by SLS (static light scattering), for example, using a Hydro 2000pP dispersant unit as described in Example 4 herein (methods for determining particle size are further described in E. Lindblad, Immunology and Cell Biology (2004) 82: 497-505). The scattering intensity is a function of the molecular weight and concentration. In one aspect, the present invention provides detoxified pneumolysin adsorbed onto aluminium phosphate, wherein greater than 80% (suitably more than 81%, 82%, 83%, 84%, 85%, 86%, 87%, 88%, 89% or 90%) of the particles of detoxified pneumolysin adsorbed onto aluminium phosphate have a size less than 10μm. In one aspect, the detoxified pneumolysin is unconjugated detoxified pneumolysin. In another aspect, the detoxified pneumolysin is conjugated detoxified pneumolysin.

Process for Adsorption

The present invention provides a process for adsorption of detoxified pneumolysin onto aluminium phosphate comprising the step of (i) admixing detoxified pneumolysin and the aluminium phosphate at a pH less than 6.5 (e.g. less than 6.4, less than 6.3, less than 6.2, less than 6.1), suitably less than pH 6.0, for example pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, or pH 5.4 to 5.6 (e.g. pH 5.5). Suitably, the ratio of dPly:Al$^+$ (from aluminium phosphate) in step (i) is between 1:1.5 to 1:5.5, between 1:1.5 to 1:4, between 1:1.5 to 1:3.5, between 1:1.5 to 1:2.5, between 1:2 to 1:2.5 (e.g. 1:2); or between 1:2.5 to 1:3.5, between 1:3 to 1:3.5 (e.g. 1:3), or between 1:3 to 1:4 (e.g. 1:3.5) (w/w; weight/weight). In one aspect, dPly is adsorbed onto aluminium phosphate in a ratio of 1 μg of dPly to 3 μg of Al' (from aluminium phosphate). In one embodiment, the pH is 5.4 to 6.2 (e.g. pH5.5+/−0.1) and the ratio of dPly:Al$^+$ is between 1:2.5 to 1:3.5 (e.g. 1:3) (w/w; weight/weight). In another embodiment, the pH is 5.4 to 6.2 (e.g. pH6.1+/−0.1) and the ratio of dPly:Al$^+$ is between 1:1.5 to 1:3.5 (e.g. 1:2.5) (w/w; weight/weight). In another embodiment, the pH is 5.4 to 6.2 (e.g. pH6.1+/−0.1) and the ratio of dPly:Al$^+$ is between 1:3 to 1:4 (e.g. 1:3.5) (w/w; weight/weight). Unless otherwise stated, such ranges are inclusive of the end points. In another embodiment, the ratio of dPly:Al$^+$ (from aluminium phosphate) in step (i) is between 1:1.5 to 1:5.5, between 1:1.5 to 1:4, between 1:1.5 to 1:3.5, between 1:1.5 to 1:2.5, between 1:2 to 1:2.5; or between 1:2.5 to 1:3.5, between 1:3 to 1:3.5, or between 1:3 to 1:4 (w/w; weight/weight) not including the end points.

Suitably, for conjugated detoxified pneumolysin, the ratio of polysaccharide:Al' (from aluminium phosphate) in step (i) is between 1:6 to 1:14, between 1:7 to 1:13, between 1:7.5 to 1:12.5, between 1:8 to 1:12 (e.g. 1:10) (w/w; weight/weight). In another aspect, conjugated dPly is adsorbed onto aluminium phosphate in a ratio of 1 μg of polysaccharide to 10 μg of Al' (from aluminium phosphate). In one embodiment, the pH is 5.4 to 6.2 (e.g. pH6.1+/−0.1) and the ratio of polysaccharide:Al' is between 1:7.5 to 1:12.5 (e.g. 1:10) (w/w; weight/weight).

Suitably, step (i) is carried out at room temperature (18-24° C.). Suitably, step (i) is carried out with stirring at between 60 to 150 rpm, such as 120 to 140 rpm (e.g. 130 rpm). Suitably, step (i) is carried out for between 10 minutes to 2 weeks, for example, 10 minutes to 5 hours, 1 to 5 hours, or 2 to 3 hours. Unless otherwise stated, such ranges are inclusive of the end points. In another embodiment, the pH is maintained (and the further mixing continues) at this pH (i.e. the pH for adsorption) for between 10 minutes to 2 weeks, for example, 10 minutes to 5 hours, 1 to 5 hours, or 2 to 3 hours not including the end points. In an embodiment of step (i), the detoxified pneumolysin and the aluminium phosphate (and optionally a buffer) are initially mixed and subsequently (e.g. after 5-15 minutes) the pH is adjusted to a pH less than 6.5 (e.g. less than 6.4, less than 6.3, less than 6.2, less than 6.1), suitably less than pH 6.0, for example pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, or pH 5.4 to 5.6 (e.g. pH 5.5) (the pH for adsorption) followed by further mixing. The pH may be adjusted using sodium hydroxide (NaOH (aq)) and hydrochloric acid (HCl (aq)). Suitably, the pH is maintained (and the further mixing continues) at this pH (i.e. the pH for adsorption) for between 10 minutes to 2 weeks, for example, 10 minutes to 5 hours, 1 to 5 hours, or 2 to 3 hours. Unless otherwise stated, such ranges are inclusive of the end points. In another embodiment, the pH is maintained (and the further mixing continues) at this pH (i.e. the pH for adsorption) for between 10 minutes to 2 weeks, for example, 10 minutes to 5 hours 1 to 5 hours, or 2 to 3 hours not including the end points.

In an aspect of the invention, the process of the invention (i.e. adsorption of dPly, step (i)), is carried out in the presence of a buffer, such as phosphate buffer (e.g. NaK$_2$). In one aspect, the concentration of the buffer (e.g. NaK$_2$) is at least 1 mM (e.g. at least 1.5 mM, 2 mM, 2.3 mM, 3 mM, 4 mM) and is suitably at most 10 mM (e.g. at most 9 mM, 8 mM, 7 mM, 6 mM, 5 mM). In another aspect the concentration of the buffer (e.g. NaK2) is between 1 mM and 5 mM, or between 1 and 4 mM, or between 1 mM and 3 mM (e.g. between 2 mM and 3 mM), for example, between 2 mM and 2.4 mM, e.g. 2 mM. The phosphate buffer, NaK2, used in the adsorption of dPly may comprise (sodium phosphate monobasic) NaH$_2$PO$_4$ and (potassium phosphate dibasic) K$_2$HPO$_4$. Suitably, the buffer has a pH 6.5 to 7.5 (e.g. pH 7.15). Unless otherwise stated, such ranges are inclusive of the end points. In another embodiment, the concentration of the buffer (e.g. NaK2) is between 1 mM and 5 mM, or between 1 and 4 mM, or between 1 mM and 3 mM (e.g. between 2 mM and 3 mM) not including the end points.

In an aspect of the invention, the process of the invention (i.e. adsorption of dPly, step (i)), is carried out in the presence of a sodium salt, e.g. NaCl. In one aspect, the concentration of the sodium salt is between 20 to 160 mM, 30 to 150 mM, 40 to 65 mM, 45 to 65 mM, 50 to 60 mM (e.g. 55 mM). Unless otherwise stated, such ranges are inclusive of the end points. In another embodiment, the concentration of the sodium salt is between 20 to 160 mM, 30 to 150 mM, 40 to 65 mM, 45 to 65 mM, 50 to 60 mM not including the end points.

In an aspect of the invention, the process further comprises the step (ii) adjustment of the pH of the composition to a pH between 6 and 7 (for example pH 6.0 to 6.5, pH 6.0 to 6.3, pH 6.1). Step (ii) is suitably carried out following step (i). Suitably, step (i) is carried out at room temperature (18-24° C.). Suitably, step (i) is carried out with stirring at between 60 to 150 rpm (e.g. 130 rpm). The pH may be adjusted using NaOH and HCl.

Following step (i) and (ii), suitably the adsorbed dPly is maintained at a pH between 6 and 7 (for example pH 6.0 to 6.5, pH 6.0 to 6.3, pH 6.1) for at least 7 days, suitably at 2-8° C. (maturation step). Accordingly, immunogenic compositions of the invention may have a pH between 6 and 7 (for example pH 6.0 to 6.5, pH 6.0 to 6.3, pH 6.1).

In one embodiment, the adsorption of dPly onto aluminium phosphate (with or without sodium salt or potassium salt) is carried out in the absence of other additives, for example in the absence of histidine.

The present invention also provides a process for preparing an immunogenic composition of the invention comprising the process of the invention for adsorption of detoxified pneumolysin onto aluminium phosphate as described herein.

Immunogenic Compositions

In an embodiment, the present invention provides an immunogenic composition comprising detoxified pneumolysin adsorbed onto aluminium phosphate prepared by the process of the invention.

In one aspect, the present invention provides an immunogenic composition comprising detoxified pneumolysin adsorbed onto aluminium phosphate, wherein more than 85% (suitably more than 90%, 91%, 92%, 93%, 94%, 95%, 96%, 97%, 98% or 99%) of the detoxified pneumolysin is adsorbed onto the aluminium phosphate. In another aspect, the present invention provides an immunogenic composition wherein greater than 80% (suitably more than 81%, 82%, 83%, 84%, 85%, 86%, 87%, 88%, 89% or 90%) of the particles of detoxified pneumolysin adsorbed onto aluminium phosphate have a size less than 10μm. In an embodiment, the pH of the immunogenic composition is between pH6 and pH7 (for example pH 6.0 to 6.5, pH 6.0 to 6.2, pH 6.1). Immunogenic compositions may be buffered at this pH, e.g. using a phosphate buffer. In one aspect, the detoxified pneumolysin in the immunogenic composition is unconjugated detoxified pneumolysin. In another aspect, the detoxified pneumolysin in the immunogenic is conjugated detoxified pneumolysin.

The immunogenic composition of the invention (i.e. comprising adsorbed dPly), may also comprise a buffer, such as phosphate buffer (e.g. $NaK_2$). In one aspect, the concentration of the buffer (e.g. $NaK_2$) is at least 1 mM (e.g. at least 1.5 mM, 2 mM, 2.3 mM, 3 mM, 4 mM) and is suitably at most 10 mM (e.g. at most 9 mM, 8 mM, 7 mM, 6 mM, 5 mM). In another aspect the concentration of the buffer (e.g. $NaK_2$) is between 1 mM and 5 mM, or between 1 mM and 3 mM (e.g. between 2 mM and 3 mM), for example, between 2 mM and 2.4 mM. The phosphate buffer, $NaK_2$, used in the adsorption of dPly may comprise (sodium phosphate monobasic) $NaH_2PO_4$ and (potassium phosphate dibasic) $K_2HPO_4$. Other buffers that could be used include histidine, sodium phosphate, potassium phosphate, carbonate, $NaHCO_3$ buffers. Other buffers that could be used also include maleate, succinate, tartrate and Tris-Maleate buffers.

In an aspect of the invention, the immunogenic composition of the invention (i.e. comprising adsorbed dPly), may also comprise a sodium salt, e.g. NaCl. In one aspect, the concentration of the sodium salt is between 20 to 160 mM, 30 to 150 mM, 40 to 65 mM, 45 to 65 mM, 50 to 60 mM (e.g. 55 mM). In another aspect, the concentration of the sodium salt is between 100 to 200 mM, 120 to 180 mM, 140 to 160 mM (e.g. 150 mM). Unless otherwise stated, such ranges are inclusive of the end points. In another embodiment, the concentration of the sodium salt is between 20 to 160 mM, 30 to 150 mM, 40 to 65 mM, 45 to 65 mM, 50 to 60 mM not including the end points.

In a further aspect, the immunogenic composition comprises less than 2 $mgAl^{3+}$/ml, suitably between 100-2000 $\mu gAl^{3'}$/ml, 500-2000 $\mu gAl^{3'}$/ml, 800-2000 $\mu gAl^{3'}$/ml, 800-1500 $\mu gAl^{3'}$/ml, 800-1200 $\mu gAl^{3'}$/ml, 1000-2000 $\mu gAl^{3'}$/ml, 1500-2000 $\mu gAl^{3'}$/ml or 1700-2000 $\mu gAl^{3'}$/ml (aluminium, $Al^{3+}$) as aluminium phosphate. Unless otherwise stated, such ranges are inclusive of the end points. In another embodiment, the immunogenic composition comprises between 100-2000 $\mu gAl^{3'}$/ml, 500-2000 $\mu gAl^{3'}$/ml, 800-2000 $\mu gAl^{3'}$, 800-1500 $\mu gAl^{3'}$/ml, 800-1200 $\mu gAl^{3'}$/ml, 1000-2000 $\mu gAl^{3'}$/ml, 1500-2000 $\mu gAl^{3'}$/ml or 1700-2000 $\mu gAl^{3'}$/ml (aluminium, $Al^{3+}$) as aluminium phosphate, not including the end points.

In a further aspect, the immunogenic composition comprises water for injection (WFI).

Immunogenic compositions of the invention may be lyophilised or in aqueous form, i.e. solutions or suspensions. Immunogenic compositions of the invention may be lyophilised in the presence of a stabilising excipient such as sucrose or trehalose. Immunogenic compositions may be presented in vials, or they may be presented in ready filled syringes.

The present invention also provides a process for preparing an immunogenic composition comprising detoxified pneumolysin, comprising the process of the invention.

Additional Antigens

Immunogenic compositions of the present invention may comprise additional antigens capable of eliciting an immune response against a human or animal pathogen. These additional antigens include, for example, additional S. pneumoniae antigens, e.g. S. pneumoniae protein antigens. Such proteins may be used as carrier proteins, or may be present as a free protein (unconjugated), or may be present both as a carrier protein and a free protein. Where the additional antigen is a pneumococcal protein, the protein may be conjugated for example to a saccharide. In an embodiment, the immunogenic composition of the invention further comprises one or more unconjugated S. pneumoniae proteins, for example, unconjugated pneumococcal polyhistidine triad protein D (PhtD). In another embodiment, the immunogenic composition of the invention further comprises one or more conjugated S. pneumoniae proteins, for example, conjugated pneumococcal polyhistidine triad protein D (PhtD).

The additional Streptococcu pneumoniae antigens are either surface exposed, at least during part of the life cycle of the pneumococcus, or are proteins which are secreted or released by the pneumococcus. In an embodiment, the S. pneumoniae antigens are selected from the following categories, such as proteins having a Type II Signal sequence motif of LXXC (where X is any amino acid, e.g. the polyhistidine triad family (PhtX)), choline binding proteins (e.g. CbpX (choline binding protein family), PcpA (pneumococcal choline-binding protein A)), proteins having a Type I Signal sequence motif (e.g. Sp101), and proteins having a LPXTG motif (where X is any amino acid, e.g., Sp128, Sp130). Preferred examples within these categories (or motifs) are the following proteins, or immunologically functional equivalents thereof. Thus, the immunogenic composition of the invention may comprise one or more S. pneumoniae proteins selected from polyhistidine triad family (PhtX), Choline Binding Protein family (CbpX), CbpX truncates, pneumococcal autolysin family (LytX) (e.g. LytA (N-acetylmuramoyl-1-alanine amidase), LytB, LytC), LytX truncates, CbpX truncate-LytX truncate chimeric proteins, PspA (pneumococcal surface protein A), PsaA (pneumococcal surface adhesion A), Sp128, Sp101, Sp130, Sp125 and Sp133. In a further embodiment, the immunogenic composition of the invention comprises 2 or more proteins selected from the group consisting of the polyhistidine triad family (PhtX), Choline Binding Protein family (CbpX), CbpX truncates, LytX family, LytX truncates, CbpXtruncate-LytXtruncate chimeric proteins (or fusions), PspA (pneumococcal surface protein A), PsaA (pneumococcal surface adhesion A), and Sp128. In a further embodiment, the immunogenic composition comprises 2 or more proteins selected from the group consisting of the polyhistidine triad family (PhtX), Choline Binding Protein family (CbpX), CbpX truncates, LytX family, LytX truncates, CbpX truncate-LytX truncate chimeric proteins (or fusions), and Sp128.

The Pht (polyhistidine triad) family comprises proteins PhtA, PhtB, PhtD, and PhtE. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and Neisseria. In one embodiment of the invention, the immunogenic composition comprises PhtD. It is understood, however, that the terms Pht A, B, D, and E refer to proteins having sequences disclosed in the citations below as well as variants thereof that have a sequence homology that is at least 90% identical to the proteins described below, e.g. amino acids 21-838 of SEQ ID NO: 4 of WO00/37105. In an embodiment it is at least 95% identical and in another embodiment it is 97% identical to the proteins described below, e.g. amino acids 21-838 of SEQ ID NO: 4 of WO00/37105.

With regards to the PhtX proteins, PhtA is disclosed in WO 98/18930, and is also referred to Sp36. As noted herein, it is a protein from the polyhistidine triad family and has the type II signal motif of LXXC. PhtD is disclosed in WO 00/37105, and is also referred to Sp036D. As noted herein, it also is a protein from the polyhistidine triad family and has the type II LXXC signal motif. PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. A preferred immunologically functional equivalent is the protein Sp42 disclosed in WO 98/18930. A PhtB truncate (a "truncate" being part of a protein having an N-terminal and/or C-terminal deletion) (approximately 79 kD) is disclosed in WO99/15675 which is also considered a member of the PhtX family. PhtE is disclosed in WO00/30299 and is referred to as BVH-3. Where any Pht protein is referred to herein, it is meant that immunogenic fragments or fusions thereof of the Pht protein can be used.

In one embodiment, the S. pneumoniae antigen selected from member(s) of the polyhistidine triad family is PhtD. The term "PhtD" as used herein includes the full length protein with the signal sequence attached or the mature full length protein with the signal peptide (for example 20 amino acids at N-terminus) removed, and immunogenic fragments, variants and/or fusion proteins thereof, e.g. SEQ ID NO: 4 of WO00/37105. In one aspect, PhtD is the full length protein with the signal sequence attached e.g. SEQ ID NO: 4 of WO00/37105. In another aspect, PhtD is a sequence comprising the mature full length protein with the signal peptide (for example 20 amino acids at N-terminus) removed, e.g. amino acids 21-838 of SEQ ID NO: 4 of WO00/37105. Suitably, the PhtD sequence comprises an N-terminal methionine. The present invention also includes PhtD polypeptides which are immunogenic fragments of PhtD, variants of PhtD and/or fusion proteins of PhtD. For example, as described in WO00/37105, WO00/39299, U.S. Pat. No. 6,699,703 and WO09/12588.

Where immunogenic fragments of PhtD proteins are used (separately or as part of a fusion protein), these immunogenic fragments will be at least about 15, at least about 20, at least about 40, or at least about 60 contiguous amino acid residues in length, e.g. from a PhtD amino acid sequence in WO00/37105 or WO00/39299, such as SEQ ID NO: 4 of WO00/37105. In an embodiment of the invention, immunogenic fragments of PhtD protein comprise at least about 15, at least about 20, at least about 40, or at least about 60 contiguous amino acid residues of the sequence shown in SEQ ID NO: 4 of WO00/37105, wherein said polypeptide is capable of eliciting an immune response specific for said amino acid sequence. In an embodiment, the immunogenic composition of the invention comprises an immunogenic fragment of PhtD, for example described in WO09/12601, WO01/98334 and WO09/12588. Where immunogenic fragments of PhtD proteins are used (separately or as part of a fusion protein), each immunogenic fragment optionally contains one or more histidine triad motif(s) of such polypeptides. A histidine triad motif is the portion of polypeptide that has the sequence HxxHxH where H is histidine and x is an amino acid other than histidine. In an embodiment of the present invention, the or each immunogenic fragment contains exactly or at least 2, 3, 4 or 5 histidine triad motifs (optionally, with native PhtD sequence between the 2 or more triads, or intra-triad sequence) where the immunogenic fragment is more than 50, 60, 70, 80, 90 or 100% identical to a native pneumococcal intra-triad PhtD sequence (e.g. the intra-triad sequence shown in SEQ ID NO: 4 of WO00/37105). Immunogenic fragments of PhtD proteins optionally contain one or more coiled coil regions of such polypeptides. A coiled coil region is a region predicted by "Coils" algorithm Lupus, A et al (1991) Science 252; 1162-1164. In an embodiment of the present invention, each immunogenic fragment contains exactly or at least 2, 3 or 4 coiled coil regions. In an embodiment of the present invention, the or each immunogenic fragment contains exactly or at least 2, 3 or 4 coiled coil regions where the immunogenic fragment is more than 50, 60, 70, 80, 90, 95, 96 or 100% identical to a native pneumococcal PhtD sequence (e.g. the sequence shown in SEQ ID NO: 4 of WO00/37105). In another embodiment of the present invention, the immunogenic fragment includes one or more histidine triad motif as well as at least 1, 2, 3 or 4 coiled coil regions.

In the case where the PhtD polypeptide is a variant, the variation is generally in a portion thereof other than the histidine triad residues and the coiled-coil region, although variations in one or more of these regions may be made. In accordance with the present invention, a variant is a protein in which the native pneumolysin is mutated. Amino acid substitution may be conservative or non-conservative. In one aspect, amino acid substitution is conservative. Substitutions, deletions, insertions or any combination thereof may be combined in a single variant so long as the variant is an immunogenic polypeptide. Variants typically include polypeptides which share at least 80, 90, 94, 95, 98, or 99% amino acid sequence identity with a wild-type sequence. Variants of PhtD typically include any immunogenic fragment or variation of PhtD which shares at least 80, 90, 95, 96, 98, or 99% amino acid sequence identity with a wild-type PhtD sequence, e.g. SEQ ID NO: 4 of WO00/37105. In an embodiment, the present invention includes immunogenic fragments and/or variants in which several, 5 to 10, 1 to 5, 1 to 3, 1 to 2 or 1 amino acid(s) are substituted, deleted, or added in any combination. In another embodiment, the present invention includes immunogenic fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

In an embodiment of the invention, PhtD and its immunogenic fragments, variants and/or fusion proteins thereof comprise an amino acid sequence sharing at least 80, 85, 90, 95, 96, 97, 98, 99 or 100% identity with amino acid sequence 21 to 838 of SEQ ID NO:4 of WO00/37105. In another embodiment of the invention, PhtD and its immunogenic fragments, variants and/or fusion proteins thereof have an amino acid sequence sharing at least 80, 85, 90, 95, 96, 97, 98, 99 or 100% identity with amino acid sequence 21 to 838 of SEQ ID NO:4 of WO00/37105. Suitably, PhtD and its immunogenic fragments, variants and/or fusion proteins thereof comprise an amino acid sequence having an N-terminal methionine. In another embodiment of the invention, PhtD and its immunogenic fragments, variants and/or fusion proteins thereof comprise at least about 15, at least about 20, at least about 40, or at least about 60 or at least about 100, or at least about 200, or at least about 400 or at least about 800 contiguous amino acid residues of the sequence shown in SEQ ID NO: 4 of WO00/37105.

In one aspect the PhtD is conjugated to a saccharide, e.g. a capsular saccharide of S. pneumoniae. For example, PhtD may be conjugated to a capsular saccharide of S. pneumoniae selected from serotypes 1, 2, 3, 4, 5, 6A, 6B, 7F, 8, 9N, 9V, 10A, 11A, 12F, 14, 15, 17F, 18C, 19A, 19F, 20, 22F, 23F and 33F. In particular, PhtD may be conjugated to a capsular saccharide of S. pneumoniae serotype 22F. In another aspect, PhtD is unconjugated or present in the immunogenic composition as a free protein. In an aspect of the invention, more than 80% (e.g. more than 82%, 85%, 90%, 91%, 92%, 93%, 94%, 95%, 96%, 97%, 98% or 99%) of the PhtD is adsorbed onto aluminium phosphate. In another aspect of the invention, greater than 80% (e.g. more than 81%, 82%, 83%, 84%, 85%, 86%, 87%, 88%, 89% or 90%) of the particles of PhtD (e.g. unconjugated PhtD) adsorbed onto aluminium phosphate have a size less than 10μm.

The present invention also provides an immunogenic composition comprising PhtD adsorbed onto aluminium phosphate, wherein more than 85% (e.g. more than 90%, 91%, 92%, 93%, 94%, 95%, 96%, 97%, 98% or 99%) of the PhtD is adsorbed onto aluminium phosphate. The present invention also provides an immunogenic composition wherein greater than 80% (e.g. more than 81%, 82%, 83%, 84%, 85%, 86%, 87%, 88%, 89% or 90%) of the particles of PhtD adsorbed onto aluminium phosphate have has a particle a size less than 10 μm.

Concerning the Choline Binding Protein family (CbpX), members of that family were originally identified as pneumococcal proteins that could be purified by choline-affinity chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions, a proline rich region (P) and a conserved choline binding region (C), made up of multiple repeats, that comprises approximately one half of the protein. As used in this application, the term "Choline Binding Protein family (CbpX)" is selected from the group consisting of Choline Binding Proteins as identified in WO97/41151, Choline binding protein A, CbpA (also referred to as PbcA (C3-binding protein A), SpsA (*Streptococcu pneumoniae* secretory IgA binding protein), PspC (pneumococcal surface protein C)), Choline binding protein D (CbpD), and Choline binding protein G (CbpG). CbpA is disclosed in WO97/41151. CbpD and CbpG are disclosed in WO00/29434. PspC is disclosed in WO97/09994. PbcA is disclosed in WO98/21337. SpsA is a Choline binding protein disclosed in WO 98/39450. In an embodiment, the Choline Binding Proteins is CbpA. Another Choline Binding Protein is pneumococcal choline-binding protein A (PcpA) (Sanchez-Beato et al FEMS Microbiology Letters 164 (1998) 207-214).

Another preferred embodiment is CbpX truncates wherein "CbpX" is CbpA, CbpD or CbpG and "CbpX truncates" refers to CbpX proteins lacking 50% or more of the Choline binding region (C). Another preferred embodiment is PcpA truncates wherein "PcpA truncates" refers to PcpA proteins lacking 50% or more of the Choline binding region (C). In an embodiment, CbpX truncates or PcpA truncates lack the entire choline binding region. In another embodiment, the CbpX truncates or PcpA truncates lack (i) the choline binding region and (ii) a portion of the N-terminal half of the protein as well, yet retain at least one repeat region. In another embodiment, the truncate has at least 2 repeat regions. Examples of such preferred embodiments are illustrated in WO99/51266 or WO99/51188, however, other choline binding proteins lacking a similar choline binding region are also contemplated within the scope of this invention.

The LytX family is membrane associated proteins associated with cell lysis. The N-terminal domain comprises choline binding domain(s), however the LytX family does not have all the features found in the CbpA family noted herein and thus for the present invention, the LytX family is considered distinct from the CbpX family. In contrast with the CbpX family, the C-terminal domain contains the catalytic domain of the LytX protein family. The family comprises LytA, LytB and LytC. With regards to the LytX family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. A preferred member of that family is LytC.

Another preferred embodiment are LytX truncates wherein "LytX" is LytA, LytB or LytC and "LytX truncates" refers to LytX proteins lacking 50% or more of the Choline binding region. Suitably such proteins lack the entire choline binding region. Yet another preferred embodiment of this invention are CbpX truncate-LytX truncate chimeric proteins (or fusions). In an embodiment, the CbpX truncate-LytX truncate chimeric protein comprises the repeat regions of CbpX and the C-terminal portion (Cterm, i.e., lacking the choline binding domains) of LytX (e.g., LytCCterm or Sp91Cterm). In another embodiment, CbpX is selected from the group consisting of CbpA, PbcA, SpsA and PspC. In another embodiment, it is CbpA. In an embodiment, LytX is LytC (also referred to as Sp91). Another embodiment of the present invention is a PspA (pneumococcal surface protein A) or PsaA (pneumococcal surface adhesion A) truncates lacking the choline binding domain (C) and expressed as a fusion protein with LytX. In an embodiment, LytX is LytC.

PsaA (pneumococcal surface adhesion A) and transmembrane deletion variants thereof have been described by Berry & Paton, Infect Immun 1996 December;64(12):5255-62. PspA (pneumococcal surface protein A) and transmembrane deletion variants thereof have been disclosed in, for example, U.S. Pat. No. 5,804,193, WO 92/14488, and WO 99/53940. Sp128 and Sp130 are disclosed in WO00/76540. Sp125 is an example of a pneumococcal surface protein with the Cell Wall Anchored motif of LPXTG (i.e. leucine-profine-X-threonine-glycine where X is any amino acid). Any protein within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase. Sp101 is disclosed in WO 98/06734 (where it has the reference # y85993). It is characterized by a Type I signal sequence. Sp133 is disclosed in WO 98/06734 (where it has the reference # y85992). It is also characterized by a Type I signal sequence.

The *S. pneumoniae* antigens may also be beneficially combined. By combined is meant that the immunogenic composition comprises all of the proteins from within the combination, either as carrier proteins or as free proteins or a mixture of the two. For example, in a combination of two proteins as set out hereinafter, both proteins may be used as carrier proteins, or both proteins may be present as free proteins, or both may be present as carrier and as free protein, or one may be present as a carrier protein and a free protein whilst the other is present only as a carrier protein or only as a free protein, or one may be present as a carrier protein and the other as a free protein. Where a combination of three proteins is given, similar possibilities exist. Preferred combinations include, but are not limited to PhtD+CbpX repeat regions, PhtD+dPly, PhtD+Sp128, PhtD+PsaA, PhtD+PspA, PhtA+CbpX repeat regions , PhtA+CbpX repeat regions -Sp91Cterm chimeric or fusion proteins, PhtA+dPly, PhtA+Sp128, PhtA+PsaA, PhtA+PspA, CbpX repeat regions+LytC, CbpX repeat regions+PspA, CbpX repeat regions+PsaA, CbpX repeat regions+Sp128, CbpX repeat regions+LytC, CbpX repeat regions+PspA, CbpX repeat regions+PsaA, CbpX repeat regions+Sp128, CbpX repeat regions+PhtD, CbpX repeat regions+PhtA. In an embodiment, CbpX repeat regionsis from CbpA. In another embodiment, it is from CbpA. Other combinations include 3 protein combinations such as PhtD+CbpX repeat regions+dPly, and PhtA+CbpX repeat regions+PhtD. In one embodiment, the immunogenic composition comprises detoxified pneumolysin and PhtD as carrier proteins. In a further embodiment, the immunogenic composition comprises detoxified pneumolysin and PhtD as free proteins.

The immunogenic compositions of the invention may also comprise *S. pneumoniae* capsular saccharides (suitably conjugated to a carrier protein), for example as described in WO2007/071707A2. The bacterial capsular saccharide from *Streptococcu pneumoniae* may be selected from a *Streptococcu pneumoniae* serotype 1, 2, 3, 4, 5, 6A, 6B, 7A, 7B, 70, 8, 9A, 9L, 9N, 9V, 10A, 10B, 100, 10F, 11A, 11B, 11C, 11D, 11F, 12A, 12B, 12F, 13, 14, 15A, 15B, 150, 15F, 16A, 16F, 17A, 17F, 18A, 18B, 180, 18F, 19A, 19B, 190, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48 capsular saccharide. The saccharides (e.g. polysaccharides (PS)) may be derived from serotypes of pneumococcus such as serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In an embodiment, at least four serotypes are included in the composition, e.g. 6B, 14, 19F and 23F (suitably conjugated to a carrier protein). In another embodiment, at least 7 serotypes are included in the composition, e.g. 4, 6B, 9V, 14, 18C, 19F and 23F (suitably conjugated to a carrier protein). In another embodiment the immunogenic composition comprises 10 or more, 11 or more, 12 or more, 13 or more, 14 or more, 15 or more, 16 or more, 17 or more, 19 or more, or 20 capsular polysaccharides from different *S. pneumoniae* serotypes (suitably conjugated to a carrier protein). In an embodiment the immunogenic composition comprises 10 to 23 capsular polysaccharides from different *S. pneumoniae* serotypes (suitably conjugated to a carrier protein). In an embodiment, the vaccine may be an 11-valent vaccine. For example, a 11-valent vaccine may comprise polysaccharides from serotypes 1, 4, 5, 6A, 6B, 7F, 9V, 14, 18C, 19F and 23F. In an embodiment, the vaccine may be an 12-valent or 13-valent vaccine. A 12 or 13-valent paediatric (infant) vaccine may also include the 11 valent formulation supplemented with serotypes 19A, or 22F, or 15 (e.g. PS1-PD, PS4-PD, PS5-PD, PS6A-CRM197, PS6B-PD, PS7F-PD, 9V-PD, 14-PD, 18C-TT, 19A-CRM197, 19F-DT, 23F-PD), whereas a 13-valent elderly vaccine may include the 11 valent formulation supplemented with serotypes 19A and 22F, 8 and 12F, or 8 and 15, or 8 and 19A, or 8 and 22F, or 12F and 15, or 12F and 19A, or 12F and 22F, or 15 and 19A, or 15 and 22F. In an embodiment, the vaccine may be a 14-valent or 15-valent vaccine. A 14 or 15-valent paediatric vaccine may include the 11 valent formulation described above supplemented with serotypes 3, 19A and 22F; serotypes 8, 19A and 22F; serotypes 12F, 19A and 22F; serotypes 15, 19A and 22F; serotypes 3, 8, 19A and 22F; serotypes 3, 12F, 19A and 22F; serotypes 3, 15, 19A and 22F. In an embodiment, the vaccine may be a 16-valent vaccine. A 16 valent vaccine may include the 11 valent formulation described above supplemented with serotypes 3, 15B, 19A, 22F and 23F. A 16 valent vaccine may include the 11 valent formulation described above supplemented with serotypes 3, 15B, 19A, 22F and 33F. In an embodiment, the vaccine may be a 19-valent vaccine. A 19 valent vaccine may include the 11 valent formulation described above supplemented with serotypes 8, 10A, 11A, 12F, 15B, 19A, 22F and 23F. A 19 valent vaccine may include the 11 valent formulation described above supplemented with serotypes 8, 10A, 11A, 12F, 15B, 19A, 22F and 33F. In an embodiment, the vaccine may be a 20-valent vaccine. A 20 valent vaccine may include the 11 valent formulation described above supplemented with serotypes 3, 8, 10A, 11A, 12F, 15B, 19A, 22F and 23F. A 20 valent vaccine may include the 11 valent formulation described above supplemented with serotypes 3, 8, 10A, 11A, 12F, 15B, 19A, 22F and 33F. In an embodiment, the vaccine may be a 21-valent vaccine. In an embodiment, the vaccine may be a 22-valent vaccine. In an embodiment, the vaccine may be a 23-valent vaccine.

Suitably, each of the saccharides is conjugated to a carrier protein. Examples of carrier proteins which may be used in the present invention are TT, DT, CRM197, PhtD, detoxified pneumolysin and protein D. In a further embodiment, each *Streptococcu pneumoniae* capsular saccharide is conjugated to a carrier protein independently selected from the group consisting of TT, DT, CRM197, PhtD and protein D. In a further embodiment, each *Streptococcu pneumoniae* capsular saccharide is conjugated to a carrier protein independently selected from the group consisting of TT, DT, CRM197 and protein D. In an embodiment, the immunogenic composition of the invention comprises two or more different carrier proteins. In an embodiment, the immunogenic composition of the invention comprises 2, 3, 4, 5 or 6 different carrier proteins.

In an embodiment, the carrier protein is protein D from Haemophilus influenzae (PD), for example, protein D sequence from FIG. 9 (FIGS. 9a and 9b together, 364 amino acids) of EP 0594610 (SEQ ID NO: 6). Inclusion of this protein in the immunogenic composition may provide a level of protection against *Haemophilus influenzae* related otitis media (Pyrmula et. al. Lancet 367; 740-748 (2006)). The Protein D may be used as a full length protein or as a fragment (for example, Protein D may be as described in WO0056360). For example, a protein D sequence may comprise (or consist) of the protein D fragment described in EP0594610 which begins at the sequence SSHSSNMANT (SerSerHisSerSerAsnMetAlaAsnThr) (SEQ ID NO. 8), and lacks the 19 N-terminal amino acids from FIG. 9 of EP0594610, optionally with the tripeptide MDP from NS1 fused to the N-terminal of said protein D fragment (348 amino acids) (SEQ ID NO:7). In one aspect, the protein D or fragment of protein D is unlipidated. The protein D could be present in the immunogenic composition as a free protein or as a carrier protein. In one aspect, protein D is present in the immunogenic composition as free protein. In another aspect, protein D is present both as a carrier protein and as free protein. In a further aspect, protein D is present as a carrier protein for one or more of the polysaccharides. In a further aspect, 2-9 of the capsular polysaccharides selected from different serotypes are conjugated to protein D. In a further aspect, protein D is present as a carrier protein for the majority of the polysaccharides, for example 6, 7, 8, 9 or more of the polysaccharides may be conjugated to protein D.

In an embodiment, the carrier protein is CRM197. CRM197 is a non-toxic form of the diphtheria toxin but is immunologically indistinguishable from the diphtheria toxin (DT). Genetically detoxified analogues of diphtheria toxin include CRM197 and other mutants described in U.S. Pat. Nos. 4,709,017, 5,843,711, 5,601,827, and 5,917,017. CRM197 is produced by C. diphtheriae infected by the nontoxigenic phage β197tox-created by nitrosoguanidine mutagenesis of the toxigenic carynephage b (Uchida et al Nature New Biology (1971) 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology September 1983 p560-564).

In an embodiment, the carrier protein is Tetanus Toxoid (TT). Tetanus toxin is a single peptide of approximately 150 kDa, which consists of 1315 amino-acid residues. Tetanustoxin may be cleaved by papain to yield two fragments; one of them, fragment C, is approximately 50 kDa. Fragment C of TT is described in Neubauer et al. *Biochim. Biophys. Acta* 1981, 27, 141-148.

Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al Infect. Immunity, 1983 245 256. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS (4-Maleimidobutyric acid N-hydroxysuccinimide ester)) or a haloacetylated carrier protein (for example using STAB (succinimidyl (4-iodoacetyl)aminobenzoate), or SIA (succinimidyl iodoacetate), or SBAP (succinimidyl-3-(bromoacetamide)propionate)). In an embodiment, the cyanate ester (optionally made by CDAP chemistry) is coupled with hexane diamine or ADH (adipic acid dihydrazide) and the amino-derivatised saccharide is conjugated to the carrier protein using carbodiimide (e.g. 1-Ethyl-3-(3-dimethylaminopropyl)carbodiimide (EDAC or EDC)) chemistry via a carboxyl group on the protein carrier. Such conjugates are described in PCT published application WO 93/15760 Uniformed Services University and WO 95/08348 and WO 96/29094.

In one aspect of the invention, dPly is individually pre-adsorbed onto aluminium phosphate in accordance with the present invention, before it is mixed with other antigens (for example before mixing with *Streptococcu pneumoniae* protein PhtD). Thus, in an aspect of the invention, the process of the invention further comprises the step (iii) mixing the adsorbed detoxified pneumolysin with one or more antigen(s) other than detoxified pneumolysin (e.g. PhtD). In one embodiment, step (iii) is suitably carried out following step (i). In another embodiment, step (iii) is suitably carried out following step (ii). PhtD protein can be prepared and purified as described in WO2007/071710 (see Example 1b).

In one embodiment, step (iii) comprises mixing the adsorbed detoxified pneumolysin with pre-adsorbed PhtD (i.e. PhtD which has previously been adsorbed onto aluminium phosphate). The PhtD pre-adsorbed onto aluminium phosphate may have been prepared by a process using different adsorption conditions from those used for the adsorption of detoxified pneumolysin. Thus, in one aspect, the pre-adsorbed PhtD is preadsorbed onto aluminium phosphate using different adsorption conditions (e.g. a different pH and/or a different ratio of protein:$Al^{3+}$ (from aluminium phosphate)) from the adsorption conditions used for the adsorption of detoxified pneumolysin onto aluminium phosphate. For example, in one aspect, pre-adsorbed PhtD is prepared by admixing the PhtD with aluminium phosphate at pH 4.5 to 5.5, pH 4.5 to 5.4, pH 4.7 to 5.2 or pH 4.9 to 5.1 (e.g. pH 5.0) and/or using a ratio of PhtD:$Al^{3+}$ (from aluminium phosphate) of between 1:1 to 1:3, suitably between 1:1 to 1:2.5, or between 1:1.5 to 1:2.5, or between 1:2 to 1:2.5 (e.g. 1:2) (w/w; weight/weight). In another aspect, PhtD is pre-adsorbed onto aluminium phosphate at pH 4.9 to 5.1 and/or in a ratio of 1 μg of PhtD to 2 μg of Al' (from aluminium phosphate). In one aspect, the PhtD is unconjugated PhtD. In another aspect, the PhtD is conjugated PhtD. Unless otherwise stated, such ranges are inclusive of the end points. In another embodiment, pre-adsorbed PhtD is prepared by admixing the PhtD with aluminium phosphate at pH 4.5 to 5.5, pH 4.5 to 5.4, pH 4.7 to 5.2 or pH 4.9 to 5.1 and/or using a ratio of PhtD:$Al^{3+}$ (from aluminium phosphate) of between 1:1 to 1:3, suitably between 1:1 to 1:2.5, or between 1:1.5 to 1:2.5, or between 1:2 to 1:2.5 (w/w; weight/weight) not including the end points.

In an embodiment, pre-adsorption of PhtD is carried out by a process wherein the PhtD and the aluminium phosphate (and optionally a buffer) are initially mixed and subsequently (e.g. after 5-15 minutes) the pH is adjusted to pH 4.5 to 5.5, pH 4.5 to 5.4, pH 4.7 to 5.2 or pH 4.9 to 5.1 (e.g. pH 5.0) (the pH for adsorption), followed by further mixing. The pH may be adjusted using sodium hydroxide (NaOH (aq)) and hydrochloric acid (HCl (aq)). Suitably, the pH is maintained (and the further mixing continues) at this pH (i.e. the pH for adsorption) for between 10 minutes to 2 weeks, for example, 10 minutes to 5 hours, 1 to 5 hours, or 2 to 3 hours. Unless otherwise stated, such ranges are inclusive of the end points. In another embodiment, the pH is maintained (and the further mixing continues) at this pH (i.e. the pH for adsorption) for between 10 minutes to 2 weeks, for example, 10 minutes to 5 hours, 1 to 5 hours, or 2 to 3 hours not including the end points.

In an aspect of the invention, the pre-adsorption of PhtD (i.e. the admixing of PhtD with aluminium phosphate), is carried out in the presence of a buffer, such as phosphate buffer (e.g. NaK$_2$). In one aspect, the concentration of the buffer (e.g. NaK$_2$) is at least 1 mM (e.g. at least 1.5 mM, 2 mM, 2.3 mM, 3 mM, 4 mM) and is suitably at most 20 mM (e.g. at most 19 mM, 18 mM, 17 mM, 16 mM, 15 mM). In another aspect the concentration of the buffer (e.g. NaK$_2$) is between 1 mM and 25 mM, or between 5 mM and 15 mM (e.g. between 8 mM and 12 mM), for example, 10 mM. The phosphate buffer, NaK$_2$, used in the adsorption of PhtD may comprise (sodium phosphate monobasic) NaH$_2$PO$_4$.1H$_2$O and (potassium phosphate dibasic) K$_2$HPO$_4$ or K$_2$HPO$_4$.3H$_2$O. Suitably, the buffer has a pH 6.5 to 7.5 (e.g. pH 7.15). Unless otherwise stated, such ranges are inclusive of the end points. In another embodiment, the concentration of the buffer (e.g. NaK$_2$) is between 1 mM and 25 mM, or between 5 mM and 15 mM (e.g. between 8 mM and 12 mM) not including the end points.

In an aspect of the invention, following pre-adsorption of PhtD onto aluminium phosphate, the pH of the pre-adsorbed PhtD is adjusted to a pH between 6 and 7 (for example pH 5.9 to 6.5, pH 5.9 to 6.3, pH 6.0) prior to mixing the pre-adsorbed PhtD and pre-adsorbed dPly.

In another aspect of the invention, a mixture of pre-adsorbed dPly and PhtD, may be prepared, according to steps (i) to (iii) described above, prior to mixing with further antigens, e.g. S. pneumoniae capsular saccharides (suitably conjugated to a carrier protein) as described herein.

Dosage

The total content of protein antigens in the immunogenic composition or vaccine of the invention will typically be in the range 1-100 µg, or 5-80 µg, e.g. in the range 50-70 µg. In one aspect, the immunogenic composition or vaccine of the invention comprises 1 µg-50 µg (for example 26 µg-45 µg, 26 µg-40 µg, 28 µg-35 µg or around 30 µg) of detoxified pneumolysin (e.g. dPly), per human dose. In another aspect, the immunogenic composition or vaccine of the invention comprises 1 µg-50 µg (for example 26 µg-45 µg, 26 µg-40 µg, 28 µg-35 µg or around 30 µg) of each S. pneumoniae protein, per human dose. For example, the immunogenic composition or vaccine of the invention may comprise 1 µg-50 µg (for example 26 µg-45 µg, 26 µg-40 µg, 28 µg-35 µg or around 30 µg) of PhtD, per human dose.

In an embodiment, the immunogenic composition or vaccine of the invention may comprise S. pneumoniae capsular saccharides, each of which may be ata dose of between 0.1-20 µg; 0.5-10 µg; 0.5-5 µg or 1-3 µg of saccharide. In an embodiment, capsular polysaccharides may be present at different dosages, for example some capsular polysaccharides may be present at a dose of around or exactly 1 µg or some capsular polysaccharides may be present at a dose of around or exactly 3 µg. "Around" or "approximately" are defined as within 10% more or less of the given figure for the purposes of the invention.

By the term "human dose" is meant a dose which is in a volume suitable for human use. Generally this is between 0.25 and 1.5 ml, although, for administration to the skin a lower volume of between 0.05 ml and 0.2 ml may be used. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the paediatric population, a human dose may be less than 0.5 ml such as between 0.25 and 0.5 ml.

Method of Administration

The vaccine preparations containing immunogenic compositions of the present invention may be used to protect or treat a mammal, e.g. human, susceptible to infection, by means of administering said vaccine via a systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). For co-administration, the optional adjuvant may be present in any or all of the different administrations. In addition to a single route of administration, 2 different routes of administration may be used. For example, polysaccharide conjugates may be administered IM (or ID) and bacterial proteins may be administered IN (or ID). In addition, the vaccines of the invention may be administered IM for priming doses and IN for booster doses.

Following an initial vaccination, subjects may receive one or several booster immunizations adequately spaced.

Vaccine

The present invention further provides a vaccine containing the immunogenic compositions of the invention and a pharmaceutically acceptable excipient or carrier.

Pharmaceutically acceptable excipients and carriers are well known and can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example, laurel sarcosine and/or polysorbate (e.g. Tween™ 80). Examples of stabilizing agents also include poloxamer (e.g. poloxamer 124, poloxamer 188, poloxamer 237, poloxamer 338 and poloxamer 407). The phamaceutically acceptable excipient may include a non-ionic surfactant, for example polyoxyethylene sorbitan fatty acid esters, Polysorbate-80 (Tween™ 80), Polysorbate-60

(Tween™ 60), Polysorbate-40 (Tween™ 40) and Polysorbate-20 (Tween™ 20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are known in the art and are described, e.g., in Remington's Pharmaceutical Sciences, by E. W. Martin, Mack Publishing Co., Easton, Pa., 5th Edition (975).

According to a further aspect of the invention there is provided a process for making the immunogenic composition or vaccine of the invention comprising the step of mixing detoxified pneumolysin adsorbed onto aluminium phosphate according to the invention with a pharmaceutically acceptable excipient or carrier.

The vaccines of the present invention may be stored in solution or lyophilized. In an embodiment, the solution is lyophilized in the presence of a sugar such as sucrose or lactose. It is still further preferable that they are lyophilized and extemporaneously reconstituted prior to use. Lyophilizing may result in a more stable composition (vaccine) and may possibly lead to higher antibody titers in the presence of 3D-MPL and in the absence of an aluminum based adjuvant.

The vaccine or immunogenic composition of the invention may also comprise an antimicrobial, typically when package in multiple dose format. For example, the immunogenic composition or vaccine of the invention may comprise 2-phenoxyethanol.

The vaccine or immunogenic composition of the invention may also comprise a detergent e.g. polysorbate, such as Tween™ 80. Detergents are generally present at low levels e.g. <0.01%, but higher levels have been suggested for stabilising antigen formulations e.g. up to 10%.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of the immunogenic composition in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are suitably present in as little as 0.1 to 10 µg, or 0.1 to 5 µg per dose; and the polysaccharide (suitably conjugated) antigens may be present in the range of 0.01-1m, and suitably between 0.01 to 0.5 µg of saccharide per dose.

As used herein, the term "intradermal delivery" means delivery of the vaccine or immunogenic composition to the region of the dermis in the skin. However, the vaccine or immunogenic composition will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine or immunogenic composition may ultimately be located solely or primarily within the dermis, or it may ultimately be distributed within the epidermis and the dermis.

The present invention further provides an improved vaccine for the prevention or amelioration of otitis media caused by *Haemophilus influenzae* by the addition of *Haemophilus influenzae* proteins, for example protein D in conjugated form or as a free (unconjugated) protein. One or more *Moraxella catarrhalis* protein antigens can also be included in the vaccine or immunogenic composition of the invention in a free or conjugated form. Thus, the present invention is an improved method to elicit an immune response against otitis media in infants.

Examples of preferred *Moraxella catarrhalis* protein antigens which can be included in a combination vaccine or immunogenic composition of the invention (especially for the prevention of otitis media) are: outer membrane protein 106 (OMP106) [WO 97/41731 (Antex) & WO 96/34960 (PMC)]; outer membrane protein 21 (OMP21) or fragments thereof (WO 0018910); lactoferrin binding protein A (LbpA)

&/or lactoferrin binding protein B (LbpB) [WO 98/55606 (PMC)]; transferrin binding protein A (TbpA) &/or transferrin binding protein B (TbpB) [WO 97/13785 & WO 97/32980 (PMC)]; Moraxella catarrhalis CopB protein [Helminen M E, et al. (1993) Infect. Immun. 61:2003-2010]; ubiquitous surface protein A1 (UspA1) and/or ubiquitous surface protein A2 (UspA2) [WO 93/03761 (University of Texas)]; outer membrane protein CD (OmpCD); HasR (PCT/EP99/03824); PilQ (PCT/EP99/03823); outer membrane protein 85 (OMP85) (PCT/EP00/01468); lipo06 (GB 9917977.2); lipo10 (GB 9918208.1); lipo11 (GB 9918302.2); lipo18 (GB 9918038.2); outer membrane protein P6 (P6) (PCT/EP99/03038); D15 surface antigen (D15) (PCT/EP99/03822); outer membrane protein A1 (OmpA1) (PCT/EP99/06781); Hly3 (PCT/EP99/03257); and outer membrane protein E (OmpE). Examples of non-typeable Haemophilus influenzae proteins or fragments thereof which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; outer membrane protein 26 (OMP26) [WO 97/01638 (Cortecs)]; P6 [EP 281673 (State University of New York)]; TbpA and/or TbpB; H. influenzae adhesin (Hia); Haemophilus surface fibrils (Hsf); Haemophilus influenzae Hin47 protein; Haemophilus influenzae Hif protein; Haemophilus influenzae Hmw1 protein; Haemophilus influenzae Hmw2 protein; Haemophilus influenzae Hmw3 protein; Haemophilus influenzae Hmw4 protein; Haemophilus influenzae autotransporter adhesin (Hap); D15 (WO 94/12641); P2; and P5 (WO 94/26304).

Methods of Treatment and Use

The present invention provides a method for the treatment or prevention of Streptococcus pneumoniae infection in a subject in need thereof comprising administering to said subject a therapeutically effective amount of an immunogenic composition or the vaccine of the invention. The present invention also provides a method of immunising a human host against Streptococcu pneumoniae infection comprising administering to the host an immunoprotective dose of the immunogenic composition or vaccine of the invention. The present invention also provides a method of inducing an immune response to Streptococcus pneumoniae (e.g. Streptococcu pneumoniae pneumolysin) in a subject, the method comprising administering a therapeutically effective amount of the immunogenic composition or vaccine of the invention.

In an embodiment, the present invention is an improved method to elicit an immune response in infants (defined as 0-2 years old in the context of the present invention) by administering a therapeutically effective amount of an immunogenic composition or vaccine of the invention (a paediatric vaccine). In one embodiment, the vaccine is a paediatric vaccine. In one embodiment, the immune response is protective (i.e. it can prevent or reduce infection caused by S. pneumoniae).

In an embodiment, the present invention is an improved method to elicit an immune response in the elderly population (in the context of the present invention a patient is considered elderly if they are 50 years or over in age, typically over 55 years and more generally over 60 years) by administering a therapeutically effective amount of the immunogenic composition or vaccine of the invention.

In one embodiment, the present invention provides a method of protecting a subject against a disease caused by infection with Streptococcu pneumoniae, or a method of preventing infection with Streptococcu pneumoniae, or a method of reducing the severity of or delaying the onset of at least one symptom associated with an infection caused by Streptococcu pneumoniae, the methods comprising administering to a subject an immunogenic amount of an immunogenic composition or vaccine of the invention.

In an embodiment, the present invention provides immunogenic compositions and vaccines of the invention for use in the prevention or treatment of a disease caused by S. pneumoniae infection. In an embodiment, the present invention provides the use of an immunogenic composition or vaccine of the invention in the manufacture of a medicament for the prevention (or treatment) of a disease caused by S. pneumoniae infection.

The disease caused by Streptococcu pneumoniae infection may be selected from pneumonia, invasive pneumococcal disease (IPD), exacerbations of chronic obstructive pulmonary disease (eCOPD), otitis media, meningitis, bacteraemia, pneumonia and/or conjunctivitis. Where the human host is an infant (defined as 0-2 years old in the context of the present invention), the disease may be selected from otitis media, meningitis, bacteraemia, pneumonia and/or conjunctivitis. In one aspect, where the human host is an infant (defined as 0-2 years old in the context of the present invention), the disease is selected from otitis media and/or pneumonia. Where the human host is elderly (i.e. 50 years or over in age, typically over 55 years and more generally over 60 years), the disease may be selected from pneumonia, invasive pneumococcal disease (IPD), and/or exacerbations of chronic obstructive pulmonary disease (eCOPD). In one aspect, where the human host is elderly, the disease is invasive pneumococcal disease (IPD). In another aspect, where the human host is elderly, the disease is exacerbations of chronic obstructive pulmonary disease (eCOPD).

Embodiments herein relating to "vaccine compositions" of the invention are also applicable to embodiments relating to "immunogenic compositions" of the invention, and vice versa.

All references or patent applications cited within this patent specification are incorporated by reference herein.

In order that this invention may be better understood, the following examples are set forth. These examples are for purposes of illustration only, and are not to be construed as limiting the scope of the invention in any manner.

Embodiments of the invention are further described in the subsequent numbered paragraphs:

1. An immunogenic composition comprising detoxified pneumolysin adsorbed onto aluminium phosphate, wherein more than 85% (e.g. more than 90%, 91%, 92%, 93%, 94%, 95%, 96%, 97%, 98% or 99%) of the detoxified pneumolysin is adsorbed onto aluminium phosphate.
2. An immunogenic composition according to paragraph 1, wherein more than 95% of the detoxified pneumolysin is adsorbed onto aluminium phosphate
3. An immunogenic composition according to paragraph 1 or paragraph 2, wherein the immunogenic composition has a pH between 6 and 7 (e.g. pH 6.0 to 6.5, pH 6.0 to 6.2, pH 6.1).
4. An immunogenic composition according to any one of paragraphs 1 to 3, wherein greater than 80% (e.g. more than 81%, 82%, 83%, 84%, 85%, 86%, 87%, 88%, 89% or 90%) of the detoxified pneumolysin adsorbed onto aluminium phosphate has a particle size less than 10 μm.
5. An immunogenic composition according to any one of paragraphs 1 to 4, wherein greater than 85% of the detoxified pneumolysin adsorbed onto aluminium phosphate has a particle size less than 10μm.
6. An immunogenic composition according to any one of paragraphs 1 to 5, wherein the detoxified pneumolysin has been chemically detoxified.
7. An immunogenic composition according to any one of paragraphs 1 to 6, wherein the detoxified pneumolysin has been genetically detoxified.
8. An immunogenic composition according to any one of paragraphs 1 to 7, wherein the detoxified pneumolysin is unconjugated.
9. An immunogenic composition according to any one of paragraphs 1 to 8, wherein the detoxified pneumolysin is conjugated to a saccharide, for example a capsular saccharide of S. pneumoniae.
10. An immunogenic composition according to any one of paragraphs 1 to 9, further comprising PhtD adsorbed onto aluminium phosphate.
11. An immunogenic composition according to paragraph 10, wherein the PhtD is unconjugated.
12. An immunogenic composition according to paragraph 10, wherein the PhtD is conjugated to a saccharide, for example a capsular saccharide of S. pneumoniae.
13. An immunogenic composition according to any one of paragraphs 1 to 12 further comprising 10 or more S. pneumoniae capsular polysaccharides from different S. pneumoniae serotypes conjugated to carrier protein(s).
14. A process for adsorption of detoxified pneumolysin onto aluminium phosphate comprising the step of (i) admixing detoxified pneumolysin and the aluminium phosphate at a pH less than 6.5 (for example, less than pH 6.0, pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, pH 5.4 to 5.6 or pH 5.5).
15. The process according to paragraph 14 wherein the detoxified pneumolysin and aluminium phosphate are in a ratio of dPly:$Al^{3+}$ (from aluminium phosphate) in step (i) between 1:1.5 to 1:4 (e.g. 1:1.5 to 1:3.5, 1:1.5 to 1:2.5, 1:2 to 1:2.5, 1:2.5 to 1:3.5, 1:3 to 1:3.5, 1:2 or 1:3) (w/w; weight/weight).
16. The process according to any of paragraphs 14 or 15 wherein step (i) is carried out in the presence of a phosphate buffer, optionally comprising $NaH_2PO_4$ and $K_2HPO_4$, and optionally at a concentration of between 1 mM and 5 mM (e.g. between 1 mM and 3 mM, between 2 mM and 2.4 mM, or 2 mM).
17. The process according to any one of paragraphs 14 to 16 followed by step (ii) adjustment of the pH of the composition to a pH between 6 and 7 (e.g. pH 6.0 to 6.5, pH 6.0 to 6.3, or pH 6.1).
18. The process according to any one of paragraphs 14 to 17 followed by step (iii) mixing the adsorbed detoxified pneumolysin with one or more antigen(s) other than detoxified pneumolysin (e.g. PhtD).
19. The process according to paragraph 18 wherein step (iii) comprises mixing the adsorbed detoxified pneumolysin with pre-adsorbed PhtD.
20. The process according to paragraph 19 wherein pre-adsorbed PhtD is prepared by admixing PhtD with aluminium phosphate at pH 4.5 to 5.5 (e.g. pH 4.5 to 5.4, pH 4.7 to 5.2, pH 4.9 to 5.1, or pH 5.0) and/or using a ratio of PhtD:$Al^{3+}$ (from aluminium phosphate) of between 1:1 to 1:3 (e.g. 1:1 to 1:2.5, 1:1.5 to 1:2.5, 1:2 to 1:2.5, or 1:2) (w/w; weight/weight).
21. The process according to paragraph 20 wherein admixing PhtD with aluminium phosphate is carried out in the presence of a phosphate buffer, optionally comprising $NaH_2PO_4.1H_2O$, $K_2HPO_4$ and/or $K_2HPO_4.3H_2O$, and optionally at a concentration between 5 mM and 15 mM (e.g. between 8 mM and 12 mM, or 10 mM).
22. The process according to any one of paragraphs 19 to 21 wherein the PhtD is conjugated to a saccharide, for example a capsular saccharide of S. pneumoniae.
23. The process according to any one of paragraphs 19 to 21 wherein the PhtD is unconjugated.
24. The process according to any one of paragraphs 14 to 23 wherein the detoxified pneumolysin is unconjugated.
25. The process according to any one of paragraphs 14 to 23 wherein the detoxified pneumolysin is conjugated to a saccharide, for example a capsular saccharide of S. pneumoniae.
26. A process for preparing an immunogenic composition comprising detoxified pneumolysin, comprising the process of paragraphs 14 to 25.
27. An immunogenic composition according to any one of paragraphs 1 to 13 prepared by the process according to paragraphs 14 to 26.
28. A vaccine comprising the immunogenic composition of any one of paragraphs 1 to 13 or 27 and a pharmaceutically acceptable excipient or carrier.
29. A method for the treatment or prevention of Streptococcu pneumoniae infection in a subject in need thereof (e.g. human) comprising administering to said subject a therapeutically effective amount of an immunogenic composition of any of paragraphs 1 to 13 or 27 or the vaccine of paragraph 28.
30. A method of immunising a human host against Streptococcu pneumoniae infection comprising administering to the host an immunoprotective dose of the immunogenic composition of any of paragraphs 1 to 13 or 27 or vaccine of paragraph 28.
31. A method of inducing an immune response to Streptococcu pneumoniae in a subject (e.g. human), the method comprising administering a therapeutically or prophylactically effective amount of the immunogenic composition of any of paragraphs 1 to 13 or 27 or the vaccine of paragraph 28.
32. The immunogenic composition of paragraphs 1 to 13 or 27 or vaccine of paragraph 28 for use in the treatment or prevention of disease caused by Streptococcus pneumoniae infection.
33. A use of the immunogenic composition of paragraphs 1 to 13 or 27 or vaccine of paragraph 28 in the manufacture of a medicament for the treatment or prevention of a disease caused by Streptococcu pneumoniae infection.

Further embodiments of the invention are also described in the subsequent numbered paragraphs:
1a. An immunogenic composition comprising detoxified pneumolysin adsorbed onto aluminium phosphate, wherein more than 85% (e.g. more than 90%, 91%, 92%, 93%, 94%, 95%, 96%, 97%, 98% or 99%) of the detoxified pneumolysin is adsorbed onto aluminium phosphate.
2a. An immunogenic composition according to paragraph 1a, wherein the pH of the composition is between 6 and 7 (e.g. pH 6.0 to 6.5, pH 6.0 to 6.2, pH 6.1).
3a. An immunogenic composition according to paragraph 1a or paragraph 2a, wherein greater than 80% (e.g. more than 81%, 82%, 83%, 84%, 85%, 86%, 87%, 88%, 89% or 90%) of the particles of detoxified pneumolysin adsorbed onto aluminium phosphate have a size less than 10 μm.

4a. An immunogenic composition according to any one of paragraphs 1a to 3a, wherein the pneumolysin has been chemically detoxified.

5a. An immunogenic composition according to any one of paragraphs 1 a to 4a, wherein the pneumolysin has been genetically detoxified.

6a. A process for adsorption of detoxified pneumolysin onto aluminium phosphate comprising the step of (i) admixing detoxified pneumolysin and the aluminium phosphate at a pH less than 6.5 (for example, less than pH 6.0, pH 5.0 to 6.2, pH 5.0 to 6.1, pH 5.2 to 6.2, pH 5.2 to 6.1, pH 5.4 to 6.2, pH 5.4 to 6.1, pH 5.5 to 6.1, pH 5.4 to 5.9, pH 5.5 to 5.9, pH 5.4 to 5.7, pH 5.5 to 5.7, pH 5.4 to 5.6 or pH 5.5).

7a. The process according to paragraph 6a wherein the ratio of dPly:Al$^+$ (from aluminium phosphate) in step (i) is between 1:1.5 to 1:4 (e.g. 1:1.5 to 1:3.5, 1:1.5 to 1:2.5, 1:2 to 1:2.5, 1:2.5 to 1:3.5, 1:3 to 1:3.5, 1:2 or 1:3) (w/w; weight/weight).

8a. The process according to paragraph 6a or 7a step (i) is carried out in the presence of a phosphate buffer, optionally comprising NaH2PO4 and K2HPO4, and optionally at a concentration of between 1 mM and 5 mM (e.g. between 1 mM and 3 mM, between 2 mM and 2.4 mM, or 2 mM).

9a. The process according to any one of paragraphs 6a to 8a followed by step (ii) adjustment of the pH of the composition to a pH between 6 and 7 (e.g. pH 6.0 to 6.5, pH 6.0 to 6.3, or pH 6.1).

10a. The process according to any one of paragraphs 6a to 9a followed by step (iii) mixing the adsorbed detoxified pneumolysin with one or more antigen(s) other than detoxified pneumolysin (e.g. PhtD).

11a. The process according to paragraph 10a wherein step (iii) comprises mixing the adsorbed detoxified pneumolysin with pre-adsorbed PhtD.

12a. The process according to paragraph 11a wherein pre-adsorbed PhtD is prepared by admixing PhtD with aluminium phosphate at pH 4.5 to 5.5 (e.g. pH 4.5 to 5.4, pH 4.7 to 5.2, pH 4.9 to 5.1, or pH 5.0) and/or using a ratio of PhtD:Al$^{3+}$ (from aluminium phosphate) of between 1:1 to 1:3 (e.g. 1:1 to 1:2.5, 1:1.5 to 1:2.5, 1:2 to 1:2.5, or 1:2) (w/w; weight/weight).

13a. The process according to paragraph 12a wherein admixing PhtD with aluminium phosphate is carried out in the presence of a phosphate buffer, optionally comprising NaH$_2$PO$_4$.1H$_2$O, K$_2$HPO$_4$ and/or K$_2$HPO$_4$.3H$_2$O, and optionally at a concentration between 5 mM and 15 mM (e.g. between 8 mM and 12 mM, or 10 mM).

14a. A process for preparing an immunogenic composition comprising detoxified pneumolysin, comprising the process of paragraphs 6a to 13a.

15a. An immunogenic composition according to any one of paragraphs 1a to 5a prepared by the process according to paragraphs 6a to 14a.

16a. A vaccine comprising the immunogenic composition of any one of paragraphs 1a to 5a or 15a and a pharmaceutically acceptable excipient or carrier.

17a. A method for the treatment or prevention of *Streptococcu pneumoniae* infection in a subject in need thereof comprising administering to said subject a therapeutically effective amount of an immunogenic composition of any of paragraphs 1a to 5a or 15a or the vaccine of paragraph 16a.

18a. A method of immunising a human host against *Streptococcu pneumoniae* infection comprising administering to the host an immunoprotective dose of the immunogenic composition of any of paragraphs 1a to 5a or 15a or vaccine of paragraph 16a.

19a. A method of inducing an immune response to *Streptococcu pneumoniae* in a subject, the method comprising administering a therapeutically or prophylactically effective amount of the immunogenic composition of any of paragraphs 1a to 5a or 15a or the vaccine of paragraph 16a.

20a. The immunogenic composition of paragraphs 1 a to 5a or 15a or vaccine of paragraph 16a for use in the treatment or prevention of disease caused by *Streptococcu pneumoniae* infection.

21a. A use of the immunogenic composition of paragraphs 1a to 5a or 15a or vaccine of paragraph 16a in the manufacture of a medicament for the treatment or prevention of a disease caused by *Streptococcu pneumoniae* infection.

EXAMPLES

Example 1a: Adsorption of detoxified pneumolysin onto Aluminium Phosphate

Detoxification of pneumolysin using formaldehyde: A stock of purified pneumolysin at a concentration of approximately 0.4mg/mi was in 25 mM potassium phosphate buffer pH 7.0 was treated with 50 mM L-lysine and 0.1% formaldehyde (w/v) for 21 days at 40° C.

Aluminium phosphate (AlPO$_4$), 1890 μg Al$^{3+/}$ ml together with PO$_4$ (Na/K$_2$) 2 mM pH7.15 and dPly (detoxified pneumolysin) 630 μg dPly/ml (ratio 1 μg dPly/3 μg Al$^{3+}$) were mixed under magnetic stirring (130 rpm) for 5 to 15 minutes at room temperature (18-24° C.). The pH was adjusted to pH 5.5+/−0.1 with NaOH 0.05M or 0.5M/HCl 0.03M or 0.3M with magnetic stirring (130 rpm) for 5 to 15 minutes at room temperature (18-24° C.). The pH was maintained at pH 5.5+/−0.1 for 120-150 minutes at room temperature (18-24° C.) under magnetic stirring (130 rpm). The pH was then adjusted to pH 6.1+/−0.1 with NaOH 0.05M or 0.5M/HCl 0.03M or 0.3M with magnetic stirring (130 rpm) for 5 to 15 minutes at room temperature (18-24° C.). Maturation was carried out for at least 7 days at 2-8° C. (maturation step) with no agitation.

Method:

---

AlPO$_4$ (Al$^{3+}$) →1890 μg Al$^{3+/}$ml
+
PO$_4$ (Na/K$_2$) 2 mM pH 7.15
+
dPly →630 μg dPly/ml (ratio 1 μg dPly/3 μg Al$^{3+}$)
↓(stirring Magnetic - Time (min): 5-15 - Temp (° C.): Room temp 18-24° C.)
Adjust pH 5.5 +/− 0.1 with NaOH 0.05M or 0.5M/HCl 0.03M or 0.3M
↓(stirring Magnetic - Time (min): 5-15 - Temp (° C.): Room temp 18-24° C.)

Check pH and adjust if necessary
↓(stirring Magnetic - Time (min): 120-150 - Temp (° C.): Room temp 18-24° C.)
Adjust pH 6.1 +/− 0.1 with NaOH 0.05M or 0.5M/HCl 0.03M or 0.3M
↓(stirring Magnetic - Time (min): 5-15 - Temp (° C.): Room temp 18-24° C.)
Check pH and adjust if necessary
↓
Maturation: Time (min): for at least 7 days - Temp (° C.): +2 to +8 - Agitation: no
↓
Sampling Remark: the vaccine bulk is maintained under gentle stirring during all formulation process, room temperature is 18-24° C.

TABLE 1

| Ingredients | | | |
|---|---|---|---|
| Name | Component | Concentration | Other |
| Antigen | dPly | 630 μg/ml | |
| $Al^{3+}$ | from $AlPO_4$ | 1890 μg/ml | |
| NaCl | | 55 mM | |
| $PO_4$ Na/$K_2$ | $NaH_2PO_4$ $K_2HPO_4$ | 2.4 mM | |
| pH | | | 6.1(+/−0.1) |

Specifications: aluminium 0.50%, phosphate 1.59%, NaCl 0.9%.

Example 1b: Adsorption of PhtD onto Aluminium Phosphate

The PhtD was taken from storage at −70° C. and thawed in a thermostatized bath at 25° C. Aluminium phosphate ($AlPO_4$), 4000 μg $Al^{3+}$/ml together with $PO_4$ (Na/$K_2$) 10 mM pH 7.15 and PhtD 2000 μg PhtD/ml (ratio PhtD/$Al^{3+}$ 1:2) were mixed under magnetic stirring (130 rpm) for 5 to 15 minutes at room temperature (18-24° C.). The pH was adjusted to pH 5.0+/−0.1 with HCl 0.03M or 0.3M followed by magnetic stirring (130 rpm) for 120-150 minutes at room temperature (18-24° C.). The pH was then adjusted to pH 6.0+/−0.1 with NaOH 0.05M or 0.5M. Sampling was carried out followed by maturation for at least 7 days at 2-8° C. (maturation step) with no agitation.
Method:

TABLE 2

| Ingredients | | | |
|---|---|---|---|
| Name | Component | Concentration | Other |
| Antigen | PhtD | 2000 μg/ml | |
| $Al^{3+}$ | $AlPO_4$ | 4000 μg $Al^{3+}$/ml | |
| NaCl | | Residual (+/−120 mM) | |
| $PO_4$ Na/$K_2$ | $NaH_2PO_4 \cdot 2H_2O$ $K_2HPO_4$ or $K_2HPO_4 \cdot 3H_2O$ | Residual (+/−4.56 mM) | |
| pH | | | 6.0(+/−0.1) |

DPly/PhtD-$AlPO_4$ vaccine may be formulated by mixing sterile solutions of NaCl and water for injection (to reach a final concentration of 150 mM NaCl), prior to addition of the required amount of sterile $AlPO_4$ which is added to obtain a final concentration of 0.5 mg $Al^{3+}$ per unit dose (0.5 ml) of final vaccine. The mixture is stirred, the pH is adjusted to 6.1±0.1 and the adsorbed dPly and PhtD are added. After addition of the antigens monobulks, the mixture is gently stirred at room temperature and if needed, the pH is adjusted to 6.1±0.1 before storage of the final bulk in glass containers at 2-8° C.

Example 1c: Formulation of dPly and PhtD Adsorbed Onto Aluminium Phosphate

Antigen was pre-adsorbed separately on $AlPO_4$ and then pooled to get the final vaccine according to the following method:

Non pH adjusted $AlPO_4$ ($Al^{3+}$) →4000 μg $Al^{3+}$/ml
+
$PO_4$ (Na/$K_2$) 10 mM pH 7.15
+
PhtD →2000 μg PhtD/ml (ratio PhtD/$Al^{3+}$ 1:2)
↓(stirring Magnetic - Time (min): 5-15 - Temp (° C.): Room temp)
Adjust and check pH 5.0 +/− 0.1 with HCl 0.03M or 0.3M
↓(stirring Magnetic - Time (min): 120-150 - Temp (° C.): Room temp)
Adjust and check pH 6.0 +/− 0.1 with NaOH 0.05M or 0.5M
↓
Sampling
↓
Maturation: Time (min): for at least 7 days - Temp (° C.): +2 to +8 - Agitation: no The frozen bulk of PhtD (storage temperature: −70° C.) is thawed in a thermostatized bath at 25° C.
Remark: the vaccine bulk is maintained under stirring during all formulation process, room temperature is 18-24° C.

Method:

WFI (water for injection)
+
NaCl 1500 mM  → ad 150 mM
+
AlPO$_4$  →ad 1000 µg Al$^{3+}$/ml
↓(stirring Magnetic - Time (min): 5-15 - Temp (° C.): Room temp)
Adjust and check pH 6.1 +/− 0.1 with NaOH 0.05M or 0.5M/HCl 0.03M or 0.3M
↓(stirring Magnetic - Time (min): 5-15 - Temp (° C.): Room temp)
Pre-adsorbed PhtD (on AlPO$_4$)  →60 µg PhtD/ml
Pre-adsorbed dPly (on AlPO$_4$)  →60 µg dPly/ml
↓(stirring Magnetic - Time (min): 15-20 - Temp (° C.): Room temp)
Check or adjust pH 6.1 +/− 0.1 with NaOH 0.05M or 0.5M/HCl 0.03M or 0.3M
↓
Sampling
↓
Storage at Temp (° C.): +2 to +8

Remark: the vaccine bulk is maintained under stirring during all formulation process.
Note:
ad means "up to".

TABLE 3

| Ingredients | | | |
|---|---|---|---|
| Name | Component | Concentration | Other |
| Antigen | PhtD<br>dPly<br>both proteins are<br>pre-adsorbed on AlPO$_4$ | 60 µg/ml of<br>each protein<br>300 µg Al$^{3+}$/ml | 30 µg of each<br>protein per<br>human dose<br>150 µg Al$^{3+}$<br>per human<br>dose |
| Al$^{3+}$ | AlPO$_4$ | 1000 µg/ml | Total: 500 µg<br>Al$^{3+}$ per<br>human dose |
| NaCl | | 150 mM | 4.38 mg per<br>human dose |
| PO$_4$<br>Na/K$_2$ | NaH$_2$PO$_4$<br>K$_2$HPO$_4$ | Residual | |
| Water for<br>injection | | | ad 500 µl |
| pH | | | 6.1(+/−0.1) |

Example 2: Completeness of Adsorption

Method: Completeness of adsorption was measured by measuring the supernatant (SN) of centrifuged samples via Lowry. To assess the percentage of each antigen adsorbed to the adjuvant (aluminium phosphate), formulation samples (with dPly) of 250 µl were centrifuged for about 10 minutes at 6000 rpm to separate the unadsorbed protein (pellet) from the adsorbed protein (supernatant). 210 µl of the supernatant (SN1) was collected for the determination of completeness of adsorption. The protein concentration in the supernatant was determined by Lowry (see details of method below). The percentage of adsorption was determined by comparing the amount of detoxified pneumolysin protein in the supernatant after centrifugation compared to a control (unadsorbed detoxified pneumolysin). The percentage of adsorption was calculated as follows: % A=100−([PrSN]×100/[PfCtr]) where, [PrSN] is the concentration of protein in supernatant and [PfCtr] is the concentration in the corresponding unadjuvanted control.

Completeness of adsorption was measured the day of formulation (T0), after 21 days at +4° C. (T21d4° C.) and in accelerated conditions (T10d4° C+6d37° C.). In the drawings, FIG. 1 illustrates T0 data.

Adsorption of detoxified pneumolysin to aluminium phosphate under different conditions was studied. The Results are shown in FIG. 1. FIG. 1 compares completeness of adsorption of detoxified pneumolysin (dPly) onto aluminium phosphate under different pHs and ratio of dPly:Al$^+$ (from aluminium phosphate): (i) pH5.5-6.1 and ratio 1:1, (ii) pH5.5-6.1 and ratio 1:2, (iii) pH5.5 to 6.1, ratio 1:3, and (iv) pH6.5 and ratio 1:3 at T0 (the day of formulation). Two different antigen lots were tested: E-DPLY-P14 and DPLYADA007.

Conclusion: Using the process of Example 1 (pH5.5 to 6.1, ratio of dPly:Al$^+$ (from aluminium phosphate) of 1:3), completeness was improved of ~20% compared to other processes (pH5.5-6.1 and ratio of dPly:Al$^+$ (from aluminium phosphate) of 1:1; pH5.5-6.1 and ratio of dPly:Al$^+$ (from aluminium phosphate) of 1:2; pH6.5 and ratio of dPly:Al$^+$ (from aluminium phosphate) of 1:3) without addition of extra alum. A 96-99% completeness of adsorption was observed with the process of Example 1.

After 1 week storage at 37° C., the dPly remained above 95% adsorbed.

In comparison a 78-83% completeness of adsorption was obtained from adsorption at pH6.5 according to the following method:
Method:

AlPO$_4$ (Al$^{3+}$) pre-adjusted to pH 6.5 +/− 0.1
+
PO$_4$ (Na/K$_2$) 2 mM pH 7.15
+
dPly  → (ratio 1 µg dPly/3 µg Al$^{3+}$)
↓(stirring Magnetic - Time (min): 5-15 - Temp (° C.): Room temp)
Check or adjust pH 6.5 +/− 0.1 with NaOH 0.05M or 0.5M/HCl 0.03M or 0.3M
↓(stirring Magnetic - Time (min): 5-15 - Temp (° C.): Room temp)

Check or adjust pH 6.5 +/− 0.1 with NaOH 0.05M or 0.5M/HCl 0.03M or 0.3M
↓ (stirring Magnetic - Time (min): 120-150 - Temp (° C.): Room temp)
↓
Maturation: Time (min): for at least 7 days - Temp (° C.): +2 to +8 - Agitation: no
↓
Sampling Remark: the vaccine bulk is maintained under stirring (130 rpm) during all formulation process.

TABLE 4

| Ingredients | | | |
|---|---|---|---|
| Name | Component | Concentration | Other |
| Antigen | dPly | 1 µg dPly/3 µg $Al^{3+}$ | |
| $Al^{3+}$ | from $AlPO_4$ | 1 µg dPly/3 µg $Al^{3+}$ | |
| NaCl | | residual | |
| $PO_4$ Na/$K_2$ | $NaH_2PO_4$ $K_2HPO_4$ | ad to 1000 µg/m of dPly | |
| pH | | | 6.5(+/−0.1) |

Lowry Method:
1. To a 200 µl sample add 200 µl 10% SDS.
2. Add 1 ml of mixture A and shake. Rest for 10 minutes.
3. Add 100 µl of reagent B and shake. Rest for 30 minutes.
4. Place in cuvette and take reading at 750 nm Mixture $A = 50$ ml 2% $Na_2CO_3$/NaOH $0.1N +$ $$500 \, \mu l \text{ potassium tartrate } 2\% + 500 \, \mu l \, CuSO_4 \cdot 5H_2O$$

Reagent B=Folin diluted×2 in $H_2O$

Example 3: Antigenicity

The antigenic activity of adsorbed pneumolysin prepared according to Example 1 (M-dPLY-PO3 and E-DPLY-P01) was determined according to the following method:
Method: Antigenic activity was determined based on the ratio between protein content by ELISA and protein content by Lowry. Elisa was used to measure antigenicity after desorption as described below:
COATING of the wells: Polyclonal Anti-dPly guinea pig sera purified (1807 µg/ml) to 5 µg/ml were diluted 1/400 in PBS and 100 µl added to each well of a microtitre plate. The plate was then incubated for 2h at 37° C.
Four washes were then carried out using 0.9% NaCl+ 0.05% Tween™.
REFERENCE SAMPLES:
M-dPLY-P03 (534 µg dPly/ml) diluted+/−0.7 µg dPLY /ml in PBS Tween™ 20 0.05% (dilution 1/800).
E-DPLY-P01 (944 µg dPly/ml) diluted+/−0.5 µg PS /ml in PBS Tween™ 20 0.05% (dilution 1/1800)
The above two reference samples were diluted in PBS Tween™ 20 0.05% to reach a concentration of +/− dPly 0.5 µg /ml and 100 µl was added into the first and second well. 100 µl of buffer was added in other wells. A 2 fold dilution was performed from second well to $11^{th}$ well. The plate was maintained for 30 minutes at 25° C.+/−2° C. with agitation.
Four washes were then carried out using 0.9% NaCl+ 0.05% Tween™.
DETECTION: Detection was carried out using polyclonal rabbit sera anti-dPly diluted 1/1000+1% guinea pig serum negative. The plate was maintained for 30 minutes at 25° C. +/−2° C. with agitation.
Four washes were then carried out using 0.9% NaCl+ 0.05% Tween™.
CONJUGATION: Conjugation was carried out by adding anti rabbit Ig, Horseradish Peroxidase Linked F(ab') 2 fragment (from donkey (Amersham. NA 9340V) diluted 1/1000+1% guinea pig serum negative to the plate (negative control). The plate was maintained for 30 minutes at 25° C.+/−2° C. with agitation.
Four washes were then carried out using 0.9% NaCl+ 0.05% Tween™
SUBSTRATE: OPD (o-Phenylenediamine (dihydrochloride)) (Sigma P8787) was used as a chromogenic substrate. A 4 mg tablet was dissolved in 9 ml $H_2O$, and 1 ml citrate buffer 1M pH 4.2, and 5 µl $H_2O_2$ were added. 100 µl of the substrate solution was added to each well of the microtitre plate. The plate was maintained for 15 minutes at room temperature in the absence of light.
The reaction was stopped using 50 µl $H_2SO_4$ 1N. Spectrophotometer reading was carried out at 490 nm and 620 nm.
Calculation: Use of 4 parameters method via SoftMaxPro software. Only the values between 25 and 85% of reference and samples curves were taken into consideration (higher and lower asymptote of the curve)
The results are shown in FIG. 2. FIG. 2 shows Elisa recovery for dPly adsorbed onto aluminium phosphate at pH5.5 to 6.1, ratio of dPly:$Al^+$ (from aluminium phosphate) of 1:3. The bars on the left correspond to the two different antigen lots: dPly E-DPLY-P14 and on the right correspond to dPly DPLYADA007.
Conclusion: Using the process of Example 1 (pH5.5 to 6.1, ratio of dPly:$Al^+$ (from aluminium phosphate) of 1:3), the Elisa recovery was within the acceptable level.

Example 4: Particle Size

Method: Particle size was measured by SLS (static light scattering) using a Hydro 2000 µP dispersant unit (Malvern Instruments) at 20-25° C. for 20s using a circulation pump speed of 1500 rpm. Latex polymer microspheres 5µm were used as a size standard. Five measurements were used to calculate the average size distributions for each sample
The results are shown in FIG. 3. FIG. 3 compares the percentage of particles of dPly adsorbed onto aluminium phosphate less than 10µm for under different pH and ratios of dPly:$Al^+$ (from aluminium phosphate): (i) pH5.5-6.1 and ratio 1:1 and (ii) pH5.5 to 6.1, ratio 1:3. The bars from left to right correspond to T0 (time=zero), T7d4° C. (7 days at 4° C.), T7d37° C. (7 days at 37° C.), T10d4+6d37° C. (10 days at 4° C. and 6 days at 37° C.) and T21d4° C. (21 days at 4° C.).
Conclusion: Using the process of Example 1 (pH5.5 to 6.1, ratio of ratio of dPly:$Al^+$ (from aluminium phosphate)

of 1:3), on average >95% of particles of detoxified pneumolysin adsorbed onto aluminium phosphate were <10μm, within the acceptable level.

Example 5: Adsorption of Conjugated Pneumolysin and PhtD onto Aluminium Phosphate The preparation of the adsorbed conjugate monobulks consisted of the separate adsorption of each of the sterile purified conjugate monobulks onto $AlPO_4$ in a ratio of 1.0 μg conjugate to 10 μg $Al^{3+}$ (as presented in Table 3) according to the method shown below. The purified conjugate monobulks were mixed to the $AlPO_4$ (previously adjusted to the serotype specific adsorption pH), and the sodium chloride 150 mM solution. The mixture was stirred during 15-45 minutes at room temperature (RT).

The mixture was next adjusted at a pH ranging from 5.2 to 6.1 (see Table 3) and gently stirred for 2 hours at room temperature for the adsorption to occur.

A final pH adjustment to 6.1±0.1 took place before storage of the adsorbed conjugate monobulks at 2-8° C. Maturation of the adsorbed conjugate monobulks lasted at least 7 days at 2-8° C.

Method:

---

$AlPO_4$ (pH preadjusted as described in Table 5)
+
Diluent NaCl 150 mM
↓
Stirring until homogenization at RT (room temperature)
↓
Add Conjugate bulk
↓
Stirring until homogenization at RT
↓
Adjust pH (pH adjustment serotype specific, Table 5)
↓
Stirring 2 h ± 15 min at RT
↓
Adjust pH 6.1 ± 0.1 pH
↓
Maturation minimum 7 days at 2-8° C.
↓
Storage at 2-8° C.

---

TABLE 5

| Serotype conjugate | pH adjustment | PS/$Al^{3+}$ ratio |
|---|---|---|
| PS19A-dPly | 6.1 | 1/10 |
| PS22F-PhtD | 6.1 | 1/10 |

Identity *S. pneumoniae* polysaccharides by ELISA:

The samples were centrifuged and the supernatants collected and stored at 2-8° C. before use. Analysis was done on the supernatant. For 19A-dPly monobulks, the microtiter plates were coated with anti-Ply guinea-pig polyclonal antibodies and incubated for 2 hours at 37° C. and for 22F-PhtD monobulks, the microtiter plates were coated with anti-PhtD guinea-pig polyclonal antibodies and incubated for 2 hours at 37° C. Plates were washed with NaCl solution containing 0.05% of polysorbate 20 (Na Tween20) after each incubation step. After washing of the plate, serial dilutions of the standard material, the internal control of the supernatant samples was prepared in phosphate-buffered saline solution supplemented with 0.05% of polysorbate 20 (PBS Tween 20). These serial dilutions were tested in duplicate. The plates are incubated overnight at 2-8° C. After washing with the NaTween 20 solution, the microtiter plates were incubated. For 19A-dPly incubation was done with rabbit anti-PS polyclonal antibodies, supplemented, if necessary, with negative guinea-pig serum for 30 minutes at 25° C. For 22F-PhtD incubation was done with rabbit anti-PS polyclonal antibodies, supplemented, if necessary, with negative guinea-pig serum for 30 minutes at 25° C. Following washing, the captured 19A-dPly antigen was incubated with goat anti-rabbit IgG conjugated to peroxidase, supplemented, if necessary, with negative guinea pig serum for 30 minutes at 25° C. The captured 22F-PhtD was incubated with a goat anti-rabbit IgG conjugated to peroxidase, supplemented, if necessary, with negative guinea-pig serum for 30 minutes at 25° C. After washing, the enzyme substrate, orthophenylenediamine supplemented with $H_2O_2$ 30%, is added. After incubation in the dark for 15 minutes at room temperature, the reaction was stopped with $H_2SO_4$ 1.0 N. The absorbance was measured by spectrophotometry at 490 nm and 620 nm. The identity was positive when the absorbances were higher than those of the background.

Total Polysaccharide Content by Resorcinol:

Dilutions of the standard material, a lot of purified polysaccharide (PS) of the concerned serotype, in NaCl 150 mM were used to establish the standard curve. The adsorbed monobulk test samples were diluted in NaCl 150 mM in order to have a content falling within the range of the standard curve. The resorcinol reagent and the sulfuric acid were added to each of the samples. After homogenization, the samples were incubated for 30 min at 100° C. For the serotype 4 and 5, the samples are incubated for 60 minutes at 100° C. The temperature of the samples was then decreased to room temperature for 30 min.

The yellow-orange colour was measured by spectrophotometry at 430 nm.

The PS Content was Calculated from the PS Standard Curve.

Completeness of Adsorption to Adjuvant (% Unbound PS):

The completeness of adsorption was determined on adsorbed monobulks by an Enzyme Linked Immunosorbent Assay (ELISA). The assay was an anti-carrier/anti-PS ELISA and the same as the one employed for the identity testing. After centrifugation of the adsorbed monobulks, the unadsorbed conjugates present in the supernatant were measured by a suitable ELISA (an anti-d Ply/anti-PS, anti-PhtD/anti-PS). The completeness of adsorption was expressed in % (amount of the conjugate measured in the supernatant to the total of PS content of the adsorbed monobulks measured by the resorcinol test).

TABLE 6

Tests for the adsorbed PS19A-dPly bulk

| Tests | D19AFAA001 |
|---|---|
| Identity S. pneumoniae polysaccharide 19A-dPly conjugate by ELISA | Positive |
| Free S. pneumoniae polysaccharide type 19A content by ELISA | <1.0% |
| Completeness of adsorption to adjuvant (% unbound S. pneumoniae polysaccharide 19A-dPly conjugate) | <1.0% |

TABLE 7

Tests for the adsorbed PS22F-PhtD bulk

| Tests | D22FHAA001 |
|---|---|
| Identity S. pneumoniae polysaccharide 22F-PhtD conjugate by ELISA | Positive |
| Free S. pneumoniae polysaccharide type 22F content by ELISA | <1.0% |
| Completeness of adsorption to adjuvant (% unbound S. pneumoniae polysaccharide 19A-dPly conjugate) | <1.0% |

SEQ ID NO.: 1
GenBank EF413952
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWNELSYDHQGKEVLTPKAWDRN
GQDLTAHFTTSIPLKGNVRNLSVKIRECTGLAWEWWRTVYEKTDLPLVRK
RTISIWGTTLYPQVEDKVEND SEQ ID NO.: 2
GenBank EF413953
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWNELSYDHQGKEVLTPKAWDRN
GQDLTAHFTTSIPLKGNVRNLSVKIRECTGLAWEWWRTVYEKTDLPLVRK
RTISIWGTTLYPQVEDKVEND SEQ ID NO.: 3
GenBank EF413954
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWDELSYDHQGKEVLTPKAWDRN
GQDLTAHFTTSIPLKGNVRNLSVKIRECTGLAWEWWRTVYEKTDLPLVRK
RTISIWGTTLYPQVEDKVEND SEQ ID NO.: 4
GenBank EF413955
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWDELSYDHQGKEVLTPKAWDRN
GQDLTAHFTTSIPLKGNVRNLSVKIRECTGLAWEWWRTVYEKTDLPLVRK
RTISIWGTTLYPQVEDKVEND SEQ ID NO.: 5
GenBank EF413959 (ply-2)
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWNELSYDHQGKEVLTPKAWDRN
GQDLTAHFTTSIPLKGNVRNLSVKIRECTGLAWEWWRTVYEKTDLPLVRK
RTISIWGTTLYPQVEDKVEND SEQ ID NO 6:
MetLysLeuLysThrLeuAlaLeuSerLeuLeuAlaAlaGlyValLeu
AlaGlyCysSerSerHisSerSerAsnMetAlaAsnThrGlnMetLys
SerAspLysIleIleIleAlaHisArgGlyAlaSerGlyTyrLeuPro
GluHisThrLeuGluSerLysAlaLeuAlaPheAlaGlnGlnAlaAsp
TyrLeuGluGlnAspLeuAlaMetThrLysAspGlyArgLeuValVal
IleHisAspHisPheLeuAspGlyLeuThrAspValAlaLysLysPhe
ProHisArgHisArgLysAspGlyArgTyrTyrValIleAspPheThr
LeuLysGluIleGlnSerLeuGluMetThrGluAsnPheGluThrLys
AspGlyLysGlnAlaGlnValTyrProAsnArgPheProLeuTrpLys
SerHisPheArgIleHisThrPheGluAspGluIleGluPheIleGln
GlyLeuGluLysSerThrGlyLysLysValGlyIleTyrProGluIle
LysAlaProTrpPheHisHisGlnAsnGlyLysAspIleAlaAlaGlu
ThrLeuLysValLeuLysLysTyrGlyTyrAspLysLysThrAspMet
ValTyrLeuGlnThrPheAspPheAsnGluLeuLysArgIleLysThr
GluLeuLeuProGlnMetGlyMetAspLeuLysLeuValGlnLeuIle -continued AlaTyrThrAspTrpLysGluThrGlnGluLysAspProLysGlyTyr TrpValAsnTyrAsnTyrAspTrpMetPheLysProGlyAlaMetAla GluValValLysTyrAlaAspGlyValGlyProGlyTrpTyrMetLeu ValAsnLysGluGluSerLysProAspAsnIleValTyrThrProLeu ValLysGluLeuAlaGlnTyrAsnValGluValHisProTyrThrVal ArgLysAspAlaLeuProGluPhePheThrAspValAsnGlnMetTyr AspAlaLeuLeuAsnLysSerGlyAlaThrGlyValPheThrAspPhe ProAspThrGlyValGluPheLeuLysGlyIleLys SEQ ID NO. 7:
MetAspProSerSerHisSerSerAsnMetAlaAsnThrGlnMetLys SerAspLysIleIleIleAlaHisArgGlyAlaSerGlyTyrLeuPro GluHisThrLeuGluSerLysAlaLeuAlaPheAlaGlnGlnAlaAsp TyrLeuGluGlnAspLeuAlaMetThrLysAspGlyArgLeuValVal IleHisAspHisPheLeuAspGlyLeuThrAspValAlaLysLysPhe ProHisArgHisArgLysAspGlyArgTyrTyrValIleAspPheThr LeuLysGluIleGlnSerLeuGluMetThrGluAsnPheGluThrLys AspGlyLysGlnAlaGlnValTyrProAsnArgPheProLeuTrpLys SerHisPheArgIleHisThrPheGluAspGluIleGluPheIleGln GlyLeuGluLysSerThrGlyLysLysValGlyIleTyrProGluIle LysAlaProTrpPheHisHisGlnAsnGlyLysAspIleAlaAlaGlu ThrLeuLysValLeuLysLysTyrGlyTyrAspLysLysThrAspMet ValTyrLeuGlnThrPheAspPheAsnGluLeuLysArgIleLysThr GluLeuLeuProGlnMetGlyMetAspLeuLysLeuValGlnLeuIle AlaTyrThrAspTrpLysGluThrGlnGluLysAspProLysGlyTyr TrpValAsnTyrAsnTyrAspTrpMetPheLysProGlyAlaMetAla GluValValLysTyrAlaAspGlyValGlyProGlyTrpTyrMetLeu ValAsnLysGluGluSerLysProAspAsnIleValTyrThrProLeu ValLysGluLeuAlaGlnTyrAsnValGluValHisProTyrThrVal ArgLysAspAlaLeuProGluPhePheThrAspValAsnGlnMetTyr AspAlaLeuLeuAsnLysSerGlyAlaThrGlyValPheThrAspPhe ProAspThrGlyValGluPheLeuLysGlyIleLys SEQ ID NO. 8:
SerSerHisSerSerAsnMetAlaAsnThr

---

The invention claimed is:

1. A process for adsorption of detoxified pneumolysin onto aluminium phosphate comprising (i) admixing detoxified pneumolysin and the aluminium phosphate at a pH less than 6.5, wherein greater than 80% of particles of the detoxified pneumolysin adsorbed onto aluminum phosphate have a particle size less than 10 μm, and (ii) mixing the adsorbed detoxified pneumolysin with one or more antigen(s) other than detoxified pneumolysin.

2. The process according to claim 1 wherein admixing (i) is followed by adjustment of the pH of a composition comprising the particles to a pH between 6 and 7.

3. The process according to claim 2 wherein admixing (i) is carried out in the presence of a phosphate buffer, optionally comprising $NaH_2PO_4$ and $K_2HPO_4$, and optionally at a concentration of between 1 mM and 5 mM.

4. The process according to claim 1 wherein admixing (i) is followed by adjustment of the pH of the composition to a pH between 6 and 7.

5. The process according to claim 1 wherein mixing the adsorbed detoxified pneumolysin with the one or more antigen(s) other than detoxified pneumolysin comprises mixing the adsorbed detoxified pneumolysin with pre-adsorbed PhtD, and wherein the pre-adsorbed PhtD is prepared by admixing PhtD with aluminium phosphate at pH 4.5 to 5.5 and/or using a ratio of PhtD:Al3+ (from aluminium phosphate) of between 1:1 to 1:3.

6. The process according to claim 1 wherein the PhtD is unconjugated or conjugated to a polysaccharide.

7. The process according to claim 1 wherein the PhtD is unconjugated or conjugated to a saccharide.

8. The process according to claim 7, wherein the PhtD is conjugated to a polysaccharide, wherein the polysaccharide is a capsular polysaccharide of *S. pneumoniae*.

9. The process according to claim 1 wherein the detoxified pneumolysin is unconjugated or conjugated to a polysaccharide.

10. The process according to claim 9, wherein the detoxified pneumolysin is conjugated to a polysaccharide, wherein the polysaccharide is a capsular polysaccharide of *S. pneumoniae*.

* * * * *

UNITED STATES PATENT AND TRADEMARK OFFICE
CERTIFICATE OF CORRECTION

PATENT NO. : 11,266,731 B2
APPLICATION NO. : 16/078225
DATED : March 8, 2022
INVENTOR(S) : Ghenne et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 701 days.

Signed and Sealed this
Thirteenth Day of December, 2022

*Katherine Kelly Vidal*

Katherine Kelly Vidal
*Director of the United States Patent and Trademark Office*